(12) United States Patent
Hayes et al.

(10) Patent No.: US 12,280,156 B2
(45) Date of Patent: Apr. 22, 2025

(54) COMPOSITIONS AND METHODS FOR TARGETED DELIVERY OF THERAPEUTIC AND/OR DIAGNOSTIC SPECIES

(71) Applicant: THE PENN STATE RESEARCH FOUNDATION, University Park, PA (US)

(72) Inventors: Daniel J. Hayes, State College, PA (US); Mohammad Abu-Laban, State College, PA (US)

(73) Assignee: THE PENN STATE RESEARCH FOUNDATION, University Park, PA (US)

(*) Notice: Subject to any disclaimer, the term of this patent is extended or adjusted under 35 U.S.C. 154(b) by 0 days.

(21) Appl. No.: 18/076,772

(22) Filed: Dec. 7, 2022

(65) Prior Publication Data

US 2023/0109863 A1   Apr. 13, 2023

Related U.S. Application Data

(63) Continuation of application No. 16/630,806, filed as application No. PCT/US2018/042017 on Jul. 13, 2018, now Pat. No. 11,559,494.

(60) Provisional application No. 62/532,536, filed on Jul. 14, 2017.

(51) Int. Cl.
*A61K 9/50* (2006.01)
*A61K 9/51* (2006.01)

(52) U.S. Cl.
CPC .......... *A61K 9/5094* (2013.01); *A61K 9/5115* (2013.01)

(58) Field of Classification Search
CPC ............................ A61K 9/5094; A61K 9/5115
See application file for complete search history.

(56) References Cited

U.S. PATENT DOCUMENTS

| 5,208,152 A | 5/1993 | Hilvert et al. |
| 2008/0226995 A1 | 9/2008 | Costanzo et al. |
| 2009/0023916 A1 | 1/2009 | Fox et al. |
| 2010/0260676 A1 | 10/2010 | Hanson |
| 2012/0302761 A1 | 11/2012 | McManus et al. |
| 2014/0017327 A1 | 1/2014 | Cheng et al. |
| 2015/0320862 A1 | 11/2015 | Ivkov et al. |
| 2016/0367671 A1 | 12/2016 | Yang et al. |
| 2017/0107538 A1 | 4/2017 | Lee et al. |

FOREIGN PATENT DOCUMENTS

| AU | 2014202199 A1 | 5/2014 |
| WO | 2008073851 A3 | 6/2008 |
| WO | 2010051530 A2 | 5/2010 |
| WO | 2010119382 A1 | 10/2010 |
| WO | 2010119389 A2 | 10/2010 |
| WO | 2012049624 A1 | 4/2012 |
| WO | 2012085789 A1 | 6/2012 |
| WO | 20120156918 A1 | 11/2012 |
| WO | 2013176845 A1 | 11/2013 |
| WO | 2016022845 A1 | 2/2016 |

OTHER PUBLICATIONS

Landry, Corey Ramaond, "An Exploration of Plasmonics for Nanoparticle-based Gene Delivery" (2015). LSU Master's These. 1167, https://digitialcommons.lsu.edu/gradschool_these/1167. (Year: 2015).
European Supplemental Search Report mailed Mar. 18, 2021, application No. 18832689.6, 9 pages.
International Search Report and Written Opinion issued in counterpart PCT Application No. PCT/IB2012/052445 dated Oct. 18, 2012 (fourteen (14) pages).
Haun, Jered B., et al. 2010. "Bioorthogonal chemistry amplifies nanoparticle binding and enhances the sensitivity of cell detection." Nat Nanotechnol. vol. 5(9): 660-665.
Rossin, Raffaella, et al. "In Vivo Chemistry for Pretargeted Tumor Imaging in Live Mice." Angew. Chem. Int. Ed. 2010, 49, 3375-3378.

*Primary Examiner* — Robert S Cabral
(74) *Attorney, Agent, or Firm* — Greenberg Traurig, LLP; Sameshnee Pelly; Ciaro Alverez-Malo

(57) ABSTRACT

In one aspect, compositions are described herein. A composition described herein comprises a nanoparticle, a therapeutic species, and a linker joining the nanoparticle to the therapeutic species. The linker joining the nanoparticle to the therapeutic species comprises a Diels-Alder cyclo-addition reaction product. Additionally, in some embodiments, the nanoparticle is a magnetic nanoparticle.

20 Claims, 14 Drawing Sheets

X: O, S, or NH*

COMPOSITIONS AND METHODS FOR TARGETED DELIVERY OF THERAPEUTIC AND/OR DIAGNOSTIC SPECIES

CROSS REFERENCE TO RELATED APPLICATIONS

This application is a continuation of U.S. patent application Ser. No. 16/630,806, filed on Jan. 13, 2020, which is a U.S. national stage application under 35 U.S.C. § 371 of PCT Patent Application No. PCT/US2018/042017, filed on Jul. 13, 2018, which claims priority pursuant to 35 U.S.C. § 119 to U.S. Provisional Patent Application Ser. No. 62/532,536, filed on Jul. 14, 2017, each of which is hereby incorporated by reference in its entirety.

STATEMENT REGARDING FEDERALLY SPONSORED RESEARCH

This invention was made with government support under Grant No. DE024790awarded by the National Institutes of Health, under Grant No. CBET1722533, awarded by the National Science Foundation and under Grant No. W81XWH-18-1-0115awarded by the U.S. Army/MRMC. The Government has certain rights in the invention.

FIELD

The invention is generally related to delivery of therapeutic and/or diagnostic species to a biological compartment, and, more specifically, to use of nanoparticles with a therapeutic agent attached with a cleavable linker.

BACKGROUND

Techniques for the stimuli-responsive delivery of therapeutic and/or diagnostic species have been of increasing interest in recent years. Several techniques have been explored, including for drug delivery. However, realizing control of drug delivery (e.g., temporal control, locational control, and/or control of the amount of drug delivered to a biological compartment) remains a significant challenge. Therefore, there is a need for improved compositions and methods for targeted delivery of therapeutic and/or diagnostic species.

SUMMARY

Compositions and methods are described herein that, in some embodiments, overcome one or more of the aforementioned deficiencies and/or concerns of prior stimuli-responsive delivery techniques. For example, in some cases, compositions and methods described herein provide improved locational control of therapeutic and/or diagnostic species delivery. In one aspect, compositions are described herein. In some instances, a composition described herein comprises a nanoparticle, a therapeutic species, and a linker joining the nanoparticle to the therapeutic species. The linker joining the nanoparticle to the therapeutic species comprises a Diels-Alder cyclo-addition reaction product.

The nanoparticle of a composition described herein can be any nanoparticle not inconsistent with the objectives of this disclosure. In some cases, for example, the nanoparticle is a metal nanoparticle. The metal nanoparticle can be formed from silver or gold, for instance. Moreover, in some embodiments, a metal nanoparticle also can have a plasmon resonant frequency in the visible or near infrared region of the electromagnetic spectrum. In other cases, the nanoparticle of a composition described herein is a magnetic nanoparticle. More particularly, in some embodiments, the magnetic nanoparticle can be formed from a magnetic metal or metal oxide. For example, a nanoparticle described herein can be formed from $Fe_2O_3$, $Fe_3O_4$, $MnFe_2O_4$, $CoFe_2O_4$, or $NiFe_2O_4$. Further, in some embodiments, the magnetic nanoparticle can exhibit a specific loss power (SLP) greater than 20 W/g at a frequency of 850 kHz and/or a specific loss power (SLP) greater than 2 W/g at a frequency of 200 kHz.

The therapeutic species of a composition described herein can be any therapeutic species not inconsistent with the objectives of this disclosure. In some embodiments, for example, the therapeutic species is a small molecule, a nucleic acid, a peptide, a protein, or any combination thereof. The nucleic acid can comprise a plasmid, a small interfering RNA ("siRNA"), a micro-RNA ("miRNA"), an miRNA mimic, or any combination thereof. Further, the therapeutic species can be covalently bound to the linker, and the linker can be covalently bound to the nanoparticle.

The linker of a composition described herein comprises or includes a Diels-Alder cycloaddition reaction product. Any such reaction product can be included in, or form at least part of, a linker described herein. For instance, in some embodiments, the Diels-Alder cycloaddition reaction product is a reaction product of a dienophile and a furan, a reaction product of a dienophile and a thiophene, or a reaction product of a dienophile and a pyrrole. Moreover, in some such cases, the Diels-Alder cyclo-addition reaction product has a retro-Diels-Alder activation temperature between 45° C. and 180° C., between 45° C. and 170° C., between 45° C. and 160° C., between 45° C. and 150° C., between 45° C. and 120° C., or between 45° C. and 80° C.

In another aspect, methods of delivering a therapeutic species to a biological compartment are described herein. In some instances, such a method comprises two steps. The first step is disposing a composition described herein in the biological compartment. Any composition described herein can be used. For example, in some cases, the composition comprises a metal or magnetic nanoparticle and a linker joining the nanoparticle to the therapeutic species, wherein the linker comprises a Diels-Alder cyclo-addition product. Turning again to exemplary methods described herein, the second step of a method can comprise initiating a retro Diels-Alder reaction to decompose the Diels-Alder cyclo-addition product of the composition. In this manner, the linker can be severed and the therapeutic species can be decoupled from the nanoparticle, including in a desired location.

Further, the step of initiating the retro Diels-Alder reaction can comprise heating the nanoparticle (e.g., a metal or magnetic nanoparticle) to an activation temperature of the retro Diels-Alder reaction, which can be between 45° C. and 160° C. In some such embodiments, the nanoparticle (e.g., a metal nanoparticle) has a plasmon resonant frequency, and heating the nanoparticle to the activation temperature comprises exposing the nanoparticle to electromagnetic radiation comprising a frequency corresponding to the plasmon resonant frequency. In other cases, the nanoparticle is a magnetic nanoparticle and heating the magnetic nanoparticle to the activation temperature comprises exposing the magnetic nanoparticle to an alternating magnetic field.

In another aspect, methods of inducing tissue regeneration are described herein. In some instances, the method comprises disposing a composition described herein in a biological compartment. In some cases, the composition comprises a metal or magnetic nanoparticle and a linker joining the nanoparticle to a therapeutic species, wherein the linker comprises a Diels-Alder cycloaddition product. Any Diels-Alder cycloaddition product described herein can be used. In some embodiments, the therapeutic species can comprise a tissue regenerative species, such as an osteogenic, chondrogenic, endotheliologenic, or myogenic modulators.

The method of inducing tissue regeneration can further comprise initiating a retro Diels-Alder reaction to decompose the Diels-Alder cycloaddition product of the composition and releasing the therapeutic species into the biological compartment. In some embodiments, the released therapeutic species induces osteogenic upregulation.

The step of initiating the retro Diels-Alder reaction can comprise heating the nanoparticle (e.g., a metal or magnetic nanoparticle) to an activation temperature of the retro Diels-Alder reaction, as previously described herein.

In another aspect, methods of treating cancer are described herein. In some instances, the method comprises disposing a composition described herein in a biological compartment. In some cases, the composition comprises a metal or magnetic nanoparticle and a linker joining the nanoparticle to a therapeutic species, wherein the linker comprises a Diels-Alder cycloaddition product. Any Diels-Alder cycloaddition product described herein can be used. In some embodiments, the therapeutic species can comprises an anti-cancer agent. Exemplary embodiments of anti-cancer agent can comprise Paclitaxil, Afatinib, Dimaleate, Bortezomib, Carfilzomib, Doxorubicin, Fluorouracil, miRNA 148b, -135, -124, -101, -29c, -15a, and -34 (MRX34) mimics.

The method of treating cancer can further comprise initiating a retro Diels-Alder reaction to decompose the Diels-Alder cycloaddition product of the composition and releasing the anti-cancer agent into the biological compartment. In some embodiments, the released therapeutic species induces cellular apoptosis, inhibits metastasis, suppresses tumor growth ("tumor suppressor"), or inhibits cancer stemness.

The step of initiating the retro Diels-Alder reaction can comprise heating the nanoparticle (e.g., a metal or magnetic nanoparticle) to an activation temperature of the retro Diels-Alder reaction, as previously described herein. These and other embodiments are described in more detail in the detailed description that follows.

BRIEF DESCRIPTION OF THE DRAWINGS

The invention will now be described by way of example, with reference to the accompanying figures, of which.

DETAILED DESCRIPTION

Figure 1:
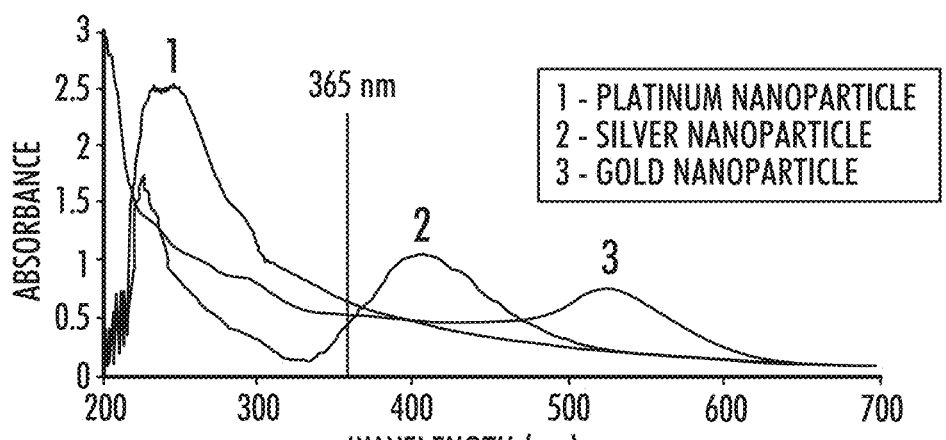
FIG. 1 illustrates absorbance spectra for metal nanoparticles.

Embodiments described herein can be understood more readily by reference to the following detailed description, examples, and figures. Elements, apparatus, and methods described herein, however, are not limited to the specific embodiments presented in the detailed description, examples, and figures. It should be recognized that these embodiments are merely illustrative of the principles of this invention. Numerous modifications and adaptations will be readily apparent to those of ordinary skill in the art without departing from the spirit and scope of the invention.

In addition, all ranges disclosed herein are to be understood to encompass any and all subranges subsumed therein. For example, a stated range of "1.0 to 10.0" should be considered to include any and all subranges beginning with a minimum value of 1.0 or more and ending with a maximum value of 10.0 or less, e.g., 1.0 to 5.3, or 4.7 to 10.0, or 3.6 to 7.9.

All ranges disclosed herein are also to be considered to include the end points of the range, unless expressly stated otherwise. For example, a range of "between 5 and 10," "from 5 to 10," or "5-10" should generally be considered to include the end points 5 and 10.

Further, when the phrase "up to" is used in connection with an amount or quantity, it is to be understood that the amount is at least a detectable amount or quantity. For example, a material present in an amount "up to" a specified amount can be present from a detectable amount and up to and including the specified amount.

I. Therapeutic and/or Diagnostic Compositions

In one aspect, compositions are described herein. In some embodiments, a composition described herein comprises (a) a nanoparticle, (b) a therapeutic species, and (c) a linker joining the therapeutic species and the nanoparticle. The linker comprises a Diels-Alder cyclo-addition reaction product. As described further herein, such a composition, in some cases, is capable of delivering a therapeutic species (or other species) to a biological compartment (or other environment). Not intending to be bound by any particular theory, it is believed that such delivery can occur when externally applied light or magnetic energy "heats" the nanoparticle, followed by transfer of thermal energy from the nanoparticle to the linker. When the transferred energy is sufficient to activate (or initiate) a retro (or reverse) Diels-Alder reaction, the result is severing of the linker and decoupling and release of the therapeutic species from the nanoparticle.

The nanoparticle, the therapeutic species, and the linker of compositions of this disclosure will now be described in further detail.

A. Nanoparticle

The nanoparticle of a composition described herein is not particularly limited and can be any nanoparticle that is not inconsistent with the objectives of this invention. For example, the nanoparticle can be a metal nanoparticle, in some embodiments, or a magnetic nanoparticle in other embodiments.

The metal nanoparticles can be formed from any suitable metal, such as any metal that can be heated by an external stimulus or signal (such as light). For example, in some instances, a nanoparticle described herein is formed from silver, gold, platinum, or a mixture or alloy thereof. In some embodiments, the metal nanoparticles are "plasmonic" metal nanoparticles, particularly metal nanoparticles having a plasmon resonant frequency at a wavelength of light suitable for use in a biological environment, such as visible light, infrared (IR) light, or near infrared (NIR). For example, the visible light in some instances is light corresponding to wavelengths from 300 nm to 700 nm; 390 nm to 700 nm; 390 nm to 600 nm; 390 nm to 500 nm; 390 nm to 450 nm; 450 nm to 700 nm; 500 nm to 650 nm; 550 nm to 600 nm; 500 nm to 700 nm; 550 nm to 650 nm; or 600 nm to 700 nm. The infrared light in some instances is light corresponding to wavelengths from 700 nm to 1 mm; 800 nm to 900 μm; 900 nm to 800 μm; 1000 μm to 700 μm; 900 μm to 800 μm; 700 nm to 900 μm; 700 nm to 800 μm; 700 nm to 700 μm; 700 nm to 600 μm; 700 nm to 500 μm; 700 nm to 400 μm; 700 nm to 300 μm; 700 nm to 200 μm; 700 nm to 100 μm; 700 nm to 1000 nm; 700 nm to 900 nm; or 700 nm to 800 nm. The near infrared light in some instances is light corresponding to wavelengths from 700 nm to 1 μm (1000 nm); 750 nm to 950 nm; 800 nm to 900 nm; 750 nm to 1 mm; 800 nm to 1 mm; 850 nm to 1 mm; 900 nm to 1 mm; 950 nm to 1 mm; 700 nm to 950 nm; 700 nm to 900 nm; 700 nm to 850 nm; 700 nm to 800 nm; or 700 nm to 750 nm.

Magnetic nanoparticles of a composition described herein can be formed from any magnetic material not inconsistent with the objectives of this disclosure. For example, in some cases, a magnetic nanoparticle is formed from a metal oxide, such as $Fe_2O_3$, $Fe_3O_4$, $MnFe_2O_4$, $CoFe_2O_4$, or $NiFe_2O_4$.

Further, nanoparticles described herein can have any size not inconsistent with the objectives of this disclosure. In some cases, a nanoparticle of a composition described herein has a size or diameter of 1-500 nm, 1-300 nm, 1-200 nm, 1-100 nm, 1-50 nm, 1-30 nm, 1-10 nm, 10-500 nm, 10-300 nm, 10-200 nm, 10-100 nm, 10-50 nm, 20-300 nm, 20-100 nm, 50-500 nm, 50-200 nm, or 50-100 nm in two dimensions or three dimensions. A population of nanoparticles of a composition described herein can also have an average size or diameter listed above.

Similarly, a nanoparticle of a composition described herein can also have any shape not inconsistent with the objectives of this disclosure. For example, in some cases, a nanoparticle described herein has a spherical or rod shape. Further, a nanoparticle can have a regular shape or an irregular shape.

Again not intending to be bound by theory, it is believed that the size, shape, and chemical composition of a nanoparticle described herein affect the nanoparticle's ability to be heated in response to an external stimulus described herein, such as the application of light, a magnetic field, or other source of energy.

This disclosure describes the use of photo-thermal and/or magneto-thermal properties of nanoparticles described herein, such as metal and/or magnetic nanoparticles. As understood by one of ordinary skill in the art, these properties refer to a nanoparticle's ability to convert light (photo) energy or magnetic (magneto) energy to thermal energy, which heats the nanoparticle. Thermal energy from the nanoparticle can then be transferred to the linker, resulting in severing of the linker and decoupling of the therapeutic species from the nanoparticle.

One example of the conversion of light energy to thermal energy occurs in plasmonic metallic nanoparticles. Plasmonic metallic nanoparticles resonate (e.g., form resonant plasmons) at discrete photonic wavelengths of applied light. These resonant plasmons can decay into photons, which heat the particle in direct proportion to the photo capture cross section and the quantum efficiency of the plasmon-to-phonon conversion. Thus, heating of the plasmonic nanoparticles occurs primarily when a wavelength of the applied light matches the unique resonant frequency of the nanoparticles and forms a resonant plasmon.

A main determinate of resonant frequency in these plasmonic metal nanoparticles is composition. For example, silver nanoparticles have a resonant frequency with a local maximum at about 420 nm, whereas gold nanoparticles resonate at about 535 nm, and platinum nanoparticles resonate at about 215 nm, as illustrated in FIG. 1.

Another determinant of resonance frequency is morphology. As an example, nanorods have multiple resonant frequencies correlating to transverse and longitudinal modes. The longitudinal modes provide red shifted resonance frequencies in the near infrared (NIR) region of the spectrum. The transverse modes have much shorter wavelengths, typically found in the optical or visible region of the electromagnetic spectrum.

Due to the discrete resonant frequencies of the plasmonic nanoparticles described herein, heating of the nanoparticles, and, as a result, severing of the linker and decoupling of the therapeutic species from the nanoparticle, can be controlled. In general, for heating of plasmonic nanoparticles to occur to a degree sufficient to sever a linker in a manner described herein, the frequency of applied light must match or substantially match a resonance frequency of the plasmonic nanoparticle.

In some embodiments, compositions described herein comprise a plurality of differing plasmonic nanoparticles. More particularly, in some cases, the differing plasmonic nanoparticles have different compositions and/or morphologies. Such nanoparticles can thus have different resonance frequencies. In these embodiments, decoupling of the therapeutic species from the nanoparticle (e.g., in a biological compartment) can be spatiotemporally controlled by using different color (frequency and wavelength) light for stimulation of the plurality of nanoparticles at different times or in different locations (e.g., different locations within the biological compartment). The different light frequencies can each match or substantially match at least one of the resonance frequencies of the different plasmonic nanoparticles.

Figure 2:
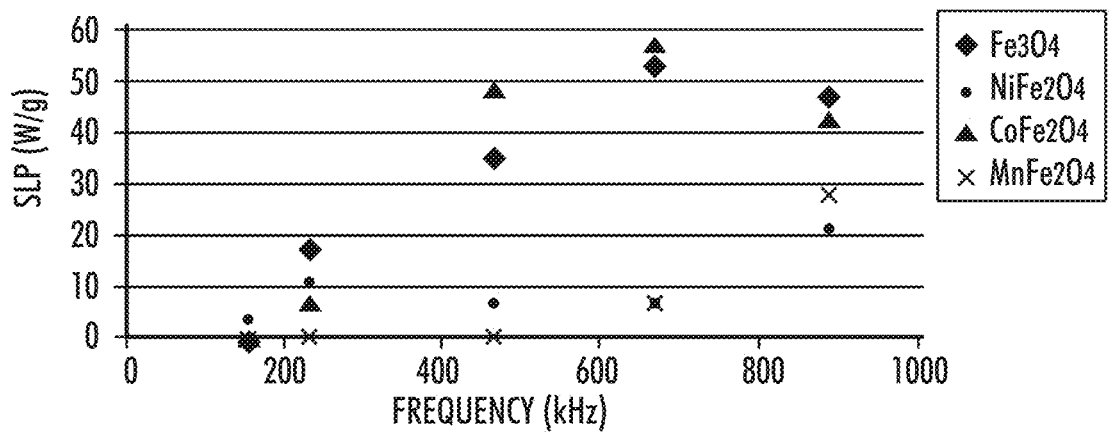
FIG. 2 illustrates a plot of specific loss power ("SLP") values for magnetic nanoparticles.
Figure 3:
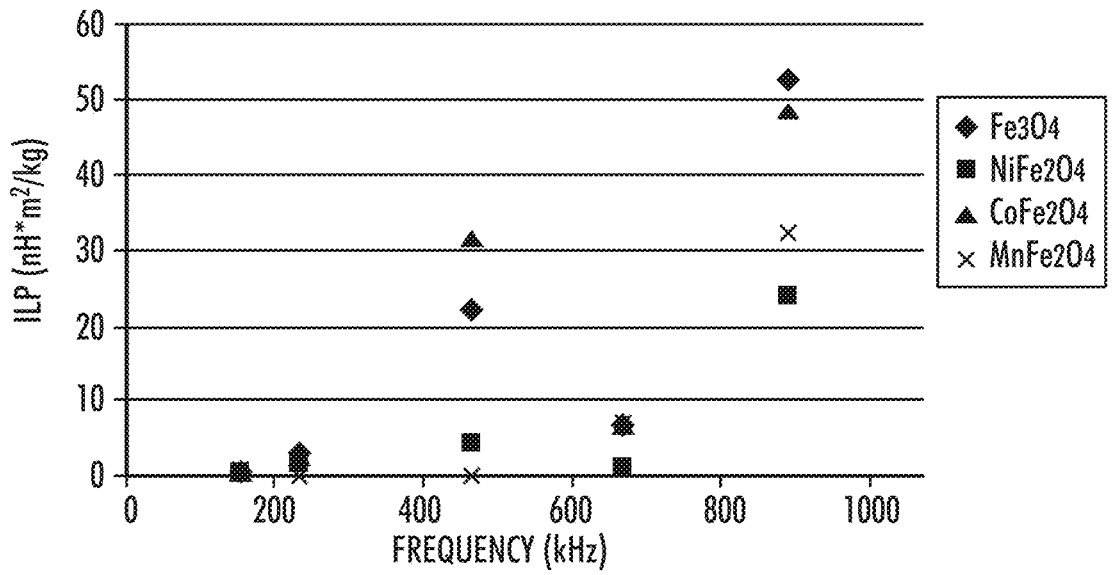
FIG. 3 illustrates a plot of intrinsic loss power ("ILP") values for magnetic nanoparticles.

Another example of the above-mentioned conversion of incident energy, external energy, or activating energy to thermal energy can occur when magnetic nanoparticles are used. Magnetic nanoparticles can convert magnetic energy from an applied alternating magnetic field to thermal energy that heats the nanoparticles. Magnetic nanoparticles, like plasmonic metal nanoparticles, can be tuned for specific loss power or to have a discrete frequency response based on their chemical composition and morphology. As understood by one of ordinary skill in the art, the specific loss power (SLP) is a figure of merit for conversion of magnetic energy from an applied alternating field into thermal energy. The higher the SLP, the greater the efficiency of conversion at a particular frequency. Depending on the frequency regime, particles can exhibit distinct SLP values based on the particles' compositions and morphology. For example, as shown in FIG. 2A, $CoFe_2O_4$ magnetic nanoparticles described herein, in some embodiments, had a higher SLP value compared to $MnFe_2O_4$, $NiFe_2O_4$, and $Fe_3O_4$ magnetic nanoparticles at a frequency of 450 and 650 kHz. Again, with reference to FIG. 2A, $Fe_3O_4$ nanoparticles had a higher SLP value, in some embodiments, at a frequency of 200 kHz than the other nanoparticles. In some embodiments, the magnetic nanoparticles described herein have an SLP value greater than 20, 25, 30, or 40 W/g at an applied alternating magnetic field frequency of 850 kHz. For example, at an applied alternating magnetic field frequency of 850 kHz, the magnetic nanoparticles have an SLP value of 20 W/g to 80 W/g; 20 W/g to 70 W/g; 20 W/g to 60 W/g; 20 W/g to 50 W/g; 20 W/g to 40 W/g; 20 W/g to 30 W/g; 30 W/g to 80 W/g; 40 W/g to 80 W/g; 50 W/g to 80 W/g; 60 W/g to 80 W/g; 70 W/g to 80 W/g; 25 W/g to 70 W/g; 30 W/g to 60 W/g; or 35 W/g to 50 W/g. Moreover, in some cases, magnetic nanoparticles described herein have an SLP value greater than 2, 5, or 10 W/g at an applied alternating magnetic field frequency of 200 kHz. For example, at an applied alternating magnetic field frequency of 200 kHz, the magnetic nanoparticles have an SLP value of 1 W/g to 20 W/g; 1 W/g to 15 W/g; 1 W/g to 10 W/g; 1 W/g to 9 W/g; 1 W/g to 8 W/g; 1 W/g to 7 W/g; 1 W/g to 6 W/g; 1 W/g to 5 W/g; 1 W/g to 4 W/g; 1 W/g to 3 W/g; 2 W/g to 12 W/g; 2 W/g to 12 W/g; 3 W/g to 12 W/g; 4 W/g to 12 W/g; 5 W/g to 12 W/g; 6 W/g to 12 W/g; 7 W/g to 12 W/g; 8 W/g to 12 W/g; 9 W/g to 12 W/g; or 10 W/g to 12 W/g.

Intrinsic loss power (ILP), as understood by one of ordinary skill in the art, is another indicator of heating efficiency at a given magnetic frequency. Higher ILP values correspond to greater heating efficiency. ILP data for nanoparticles according to some embodiments described herein are provided in FIG. 2B. In some instances, ILP values for the nanoparticles described herein range from 0.1 to 12 $nHm^2/kg$, 0.1 to 11 $nHm^2/kg$, 0.1 to 10 $nHm^2/kg$, 0.1 to 9 $nHm^2/kg$, 0.1 to 8 $nHm^2/kg$, 0.1 to 7 $nHm^2/kg$, 0.1 to 6 $nHm^2/kg$, 0.1 to 5 $nHm^2/kg$, 0.1 to 4 $nHm^2/kg$, 0.23-3.1 $nHm^2/kg$, 0.1 to 2 $nHm^2/kg$, or 0.1 to 1 $nHm^2/kg$.

B. Therapeutic Species

The therapeutic species of a composition described herein is not particularly limited. Any therapeutic species not inconsistent with the objectives of this disclosure can be used. Moreover, the therapeutic species can be any species useful for treating a disease or condition of a patient, including treating a human patient in vivo. For example, in some cases, a therapeutic species of a composition described herein is a small molecule, a nucleic acid, a peptide, a protein, or any combination thereof. The nucleic acid can comprise a plasmid, a small interfering RNA ("siRNA"), a micro-RNA ("miRNA"), an miRNA mimic, or any combination thereof. As understood by those of ordinary skill in the art, miRNA mimics are chemically modified double-stranded RNAs that mimic endogenous miRNAs and enable miRNA functional analysis by up-regulation of miRNA activity. In some embodiments, a therapeutic species described herein is an RNA sequence. The term small molecule is understood by those of ordinary skill in the art to comprise a hydrocarbon-based compound having a molecular weight between 100 daltons to 1000 daltons; 100 daltons to 900 daltons; 100 daltons to 800 daltons; 100 daltons to 700 daltons; 100 daltons to 600 daltons; 100 daltons to 500 daltons; 100 daltons to 400 daltons; 100 daltons to 300 daltons; 100 daltons to 200 daltons; 200 daltons to 900 daltons; 250 daltons to 800 daltons; 300 daltons to 700 daltons; 350 daltons to 600 daltons; 400 daltons to 500 daltons; 200 daltons to 1000 daltons; 300 daltons to 1000 daltons; 400 daltons to 1000 daltons; 500 daltons to 1000 daltons; 600 daltons to 1000 daltons; 700 daltons to 1000 daltons; 800 daltons to 1000 daltons; or 900 daltons to 1000 daltons. The small molecule can also comprise a hydrocarbon-based compound having additional heteroatoms, such as O, N, S, B, P, or any combination thereof. Additionally, the small molecule can be saturated or unsaturated, having single, double, or triple bonds. The small molecule can also in some instances be linear or cyclic (both aromatic or nonaromatic).

Additionally, in some instances, a therapeutic species of a composition described herein can be a theranostic species. Such a species can be used to diagnose a disease or condition, as well as treat the disease or condition. Non-limiting examples of theranostic species include therapeutic species described above, wherein the therapeutic species is also luminescent (e.g., fluorescent or phosphorescent), radioactive, MRI active, or otherwise capable of being imaged or tracked, including in a human patient in vivo.

In still other cases, a therapeutic or theranostic species described herein can be replaced or at least partially replaced with a diagnostic species or an imaging agent. Such a diagnostic species can be used to diagnose a disease or condition rather than treat the disease or condition. For example, in some embodiments, the diagnostic agent can be an antibody specific to biomarkers expressed in a cell. For instance, the diagnostic agent could be an antigen specific to a particular cell type or disease, such as a prostate specific antigen (PSA) to diagnose the presence of prostate cancer.

A contrast agent, in some cases, comprises a computed tomography (CT) contrast agent such as a radiocontrast agent or iodinated contrast agent. In some instances, a contrast agent comprises a magnetic resonance imaging (MRI) contrast agent, such as a positive magnetic resonance (T1) contrast agent. In some embodiments, such a positive contrast agent includes a chemical species comprising gadolinium or another lanthanide, such as gadolinium chloride. Moreover, a contrast agent suitable for use in some embodiments described herein can be a molecular contrast agent or a particulate contrast agent. A contrast agent may also be a nanoparticulate material. In some cases, a contrast agent comprises superparamagnetic iron oxide (SPIO) such as Feraheme or Ferumoxytol, gold manganese, or gadolinium. Other contrast agents may also be used.

An imaging agent, in some embodiments, comprises a luminescent species, such as a fluorescent species or phosphorescent species. In some instances, an imaging agent comprises an organic fluorophore or dye such as a rhodamine, coumarin, or cyanine (such as NIR-797). In some embodiments, an imaging agent comprises a luminescent biomolecule such as green fluorescent protein (GFP) or plasmid DNA vector encoding yellow fluorescent protein (pEYFP-N1). An imaging agent may also comprise an organic fluorophore or dye conjugated to a biomolecule, such as rhodamine conjugated bovine serum albumin (BSA-rhodamine). In still other cases, an imaging agent comprises an inorganic material such as a semiconductor nanocrystal or quantum dot, which may include a Group II-VI semiconductor nanocrystal (such as CdSe) or a Group III-V semiconductor nanocrystal (such as InP or InAs).

Moreover, an imaging agent described herein can emit light having any wavelength or luminescence profile not inconsistent with the objectives of the present disclosure. For instance, in some embodiments, an imaging agent emits light having a wavelength centered in the near-infrared region of the electromagnetic spectrum. An imaging agent may also emit light having a wavelength centered in the visible region or the non-near-infrared region of the electromagnetic spectrum. In some cases, for example, an imaging agent described herein has an emission profile centered at a wavelength between 400 nm and 700 nm, between 500 nm and 650 nm, between 600 nm and 900 nm, between 700 nm and 900 nm, between 750 nm and 850 nm, between 800 nm and 1100 nm, between 1100 nm and 1400 nm.

Figure 4:
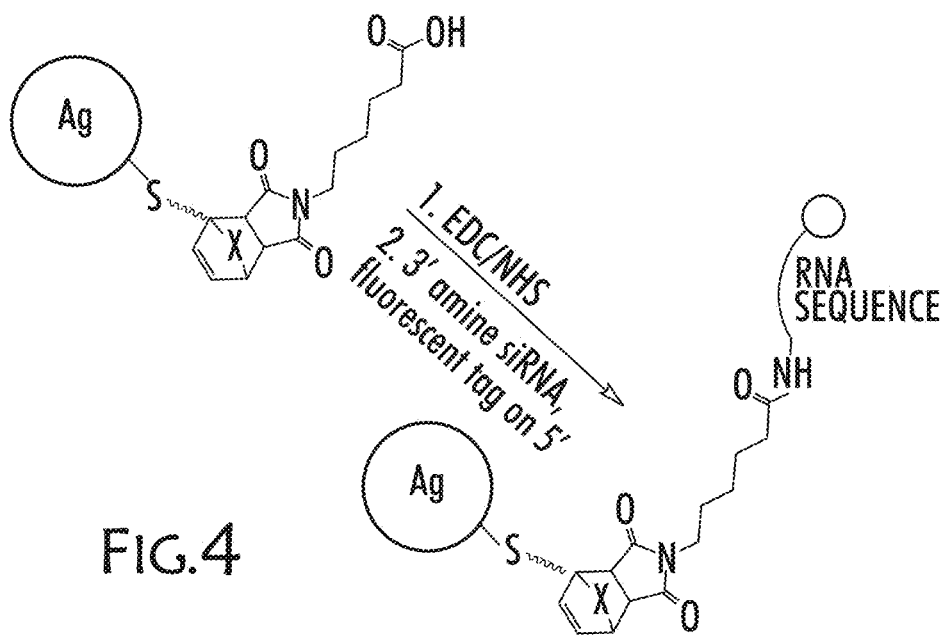
FIG. 4 schematically illustrates a linker covalently bound to a therapeutic species.
Figure 5:
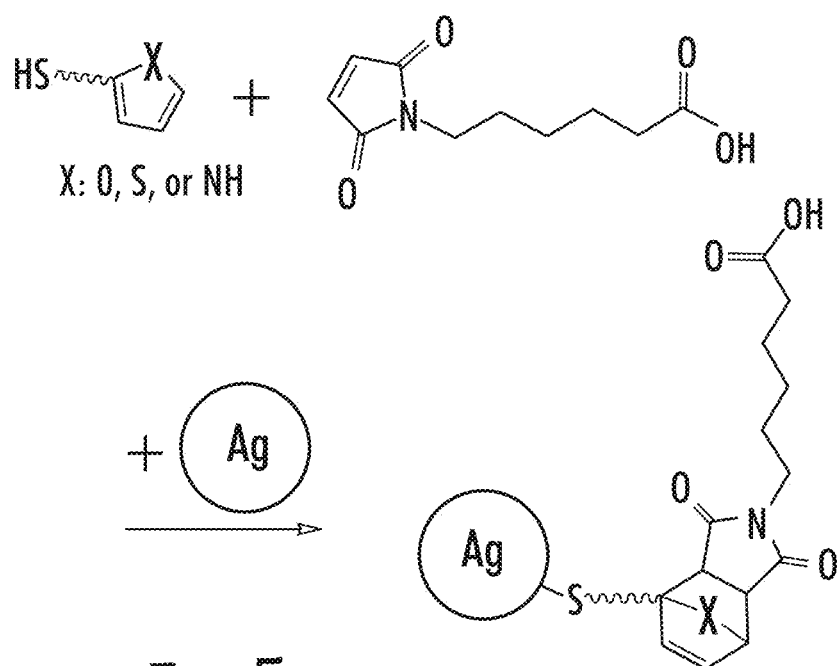
FIG. 5 schematically illustrates a Diels-Alder reaction between a diene and a dienophile 6-maleimide hexanoic acid to form a linker.

Further, a therapeutic species (or theranostic or diagnostic species or imaging agent) described herein can be connected, attached, or bonded to a linker in any manner not inconsistent with the objectives of this disclosure. In some embodiments, for instance, the therapeutic species is connected to the linker via a covalent bond. For example, an amine-terminated therapeutic species (e.g., an amine-terminated nucleic acid) can be covalently bonded to a linker by reacting the amine-terminated nucleic acid with a carboxy-terminated end of a linker via EDC (1-Ethyl-3-(3-dimethylaminopropyl)-carbodiimide) coupling or other carbodiimide coupling. Carbodiimide coupling is described in Dunetz J, Magano J, Weisenburger G., "Large-Scale Applications of Amide Coupling Reagents for the Synthesis of Pharmaceuticals," *Org. Process Res. Dev.* 2016, 20, 140-177, which is incorporated by reference in its entirety herein. FIG. 4 and FIG. 5 also illustrate such linkages. Specifically, FIG. 4 shows an exemplary EDC-coupling reaction of an amine-terminated RNA sequence being covalently bound to a carboxy-terminated end of a linker.

In some embodiments, the composition described herein is for use in tissue regeneration. In this instance, the therapeutic species is a tissue regenerative species (i.e., "tissue regenerator"). The tissue regenerative species can comprise an osteogenic modulator, a chondrogenic modulator, an endotheliologenic modulator, or a myogenic modulator. Exemplary embodiments of osteogenic modulators can comprise, simvastatin, strontium ranelate, miRNA 26a, 148b, 27a, and 489, or any osteogenic modulator not inconsistent with the objectives of this disclosure. Exemplary embodiments of chondrogenic modulators comprise, miR-9, miR-140 and miR-30A, although the chondrogenic modulator described herein can be any chondrogenic modulator not inconsistent with the objectives of this disclosure. Exemplary embodiments of endotheliogenic modulators comprise miR-210, miR-195, miR-155, miR-106b, miR-93, and miR-25, although the endotheliogenic modulator described herein can be any endotheliogenic modulator not inconsistent with the objectives of this disclosure. Exemplary embodiments of myogenic modulators comprise miR-206, miR-1, siGDF-8, miR-133, miR-24 and miR-16 although the myogenic modulator described herein can be any myogenic modulator not inconsistent with the objectives of this disclosure.

In some embodiments, the composition described herein is for use in cancer chemotherapy. In this instance, the therapeutic species can comprise an anti-cancer or anti-tumor agent (hereinafter generally called "anti-cancer"). Exemplary embodiments of anti-cancer species comprise Paclitaxil, Afatinib, Dimaleate, Bortezomib, Carfilzomib, Doxorubicin, Fluorouracil, miRNA-148b, -135, -124, -101, -29c, -15a, and -34 (MRX34) mimics or any anti-cancer agent not inconsistent with the objectives of this disclosure.

C. Linker

The linker of a composition described herein is not particularly limited and can be any linker that is not inconsistent with the objectives of this disclosure. As described above, the linker comprises a Diels-Alder cyclo-addition product. As understood by one of ordinary skill in the art, a Diels-Alder reaction is a conjugate addition reaction of a conjugated diene with a dieneophile. Moreover, the dienophile can comprise an ethyleneically unsaturated moiety. For instance, in some cases, the dienophile is a substituted or unsubstituted alkene or alkyne. In some embodiments, the Diels-Alder cyclo-addition product of a composition described herein is a reaction product of a dienophile with a furan, thiophene, or a pyrrole. An exemplary Diels-Alder reaction of a furan, thiophene, or pyrrole (each being exemplary dienes) with 6-maleimide hexanoic acid (an exemplary dienophile) is shown for example in FIG. 5.

Figure 6:
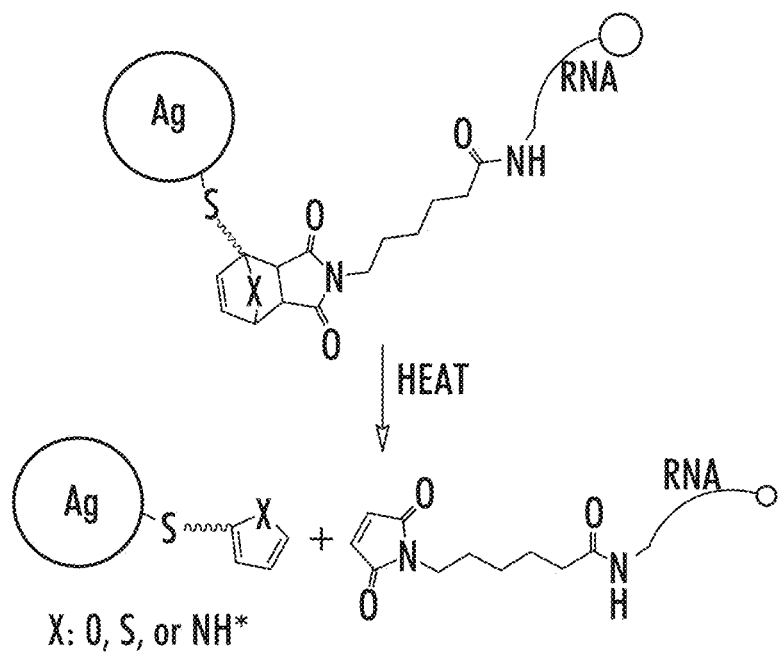
FIG. 6 schematically illustrates an exemplary retro-Diels-Alder reaction of the product of FIG. 5.

As described further herein, the Diels-Alder cyclo-addition product in the linker can undergo a retro (or reverse) Diels-Alder reaction. This retro (or reverse) Diels-Alder reaction breaks up the cyclo-addition product formed by a (forward) Diels-Alder reaction into the reaction precursors that originally formed the cyclo-addition product in the forward Diels-Alder reaction. This breaking up or cleaving of the Diels-Alder cyclo-addition product in the linker results in decoupling of the therapeutic species and the nanoparticle, as illustrated in FIG. 6.

Figure 7:
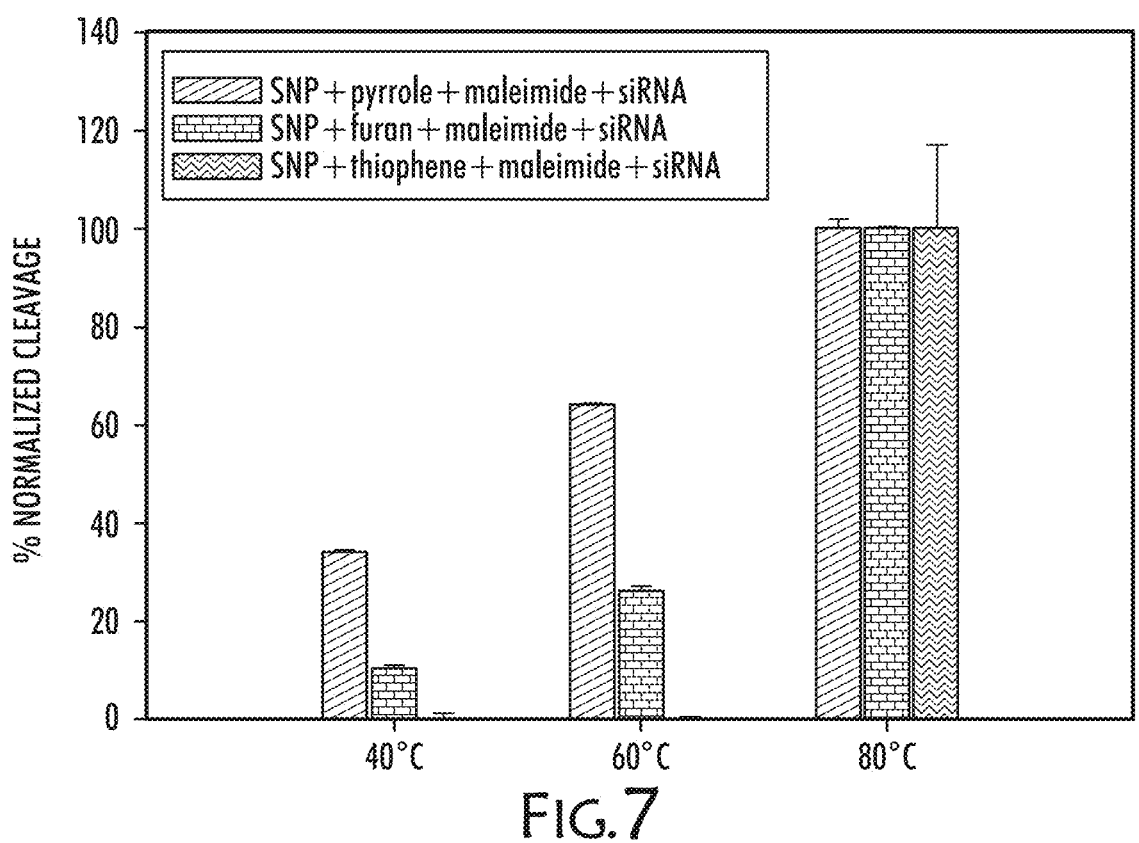
FIG. 7 graphically illustrates cleavage temperatures of different linkers in a retro-Diels-Alder reaction.
Figure 10:
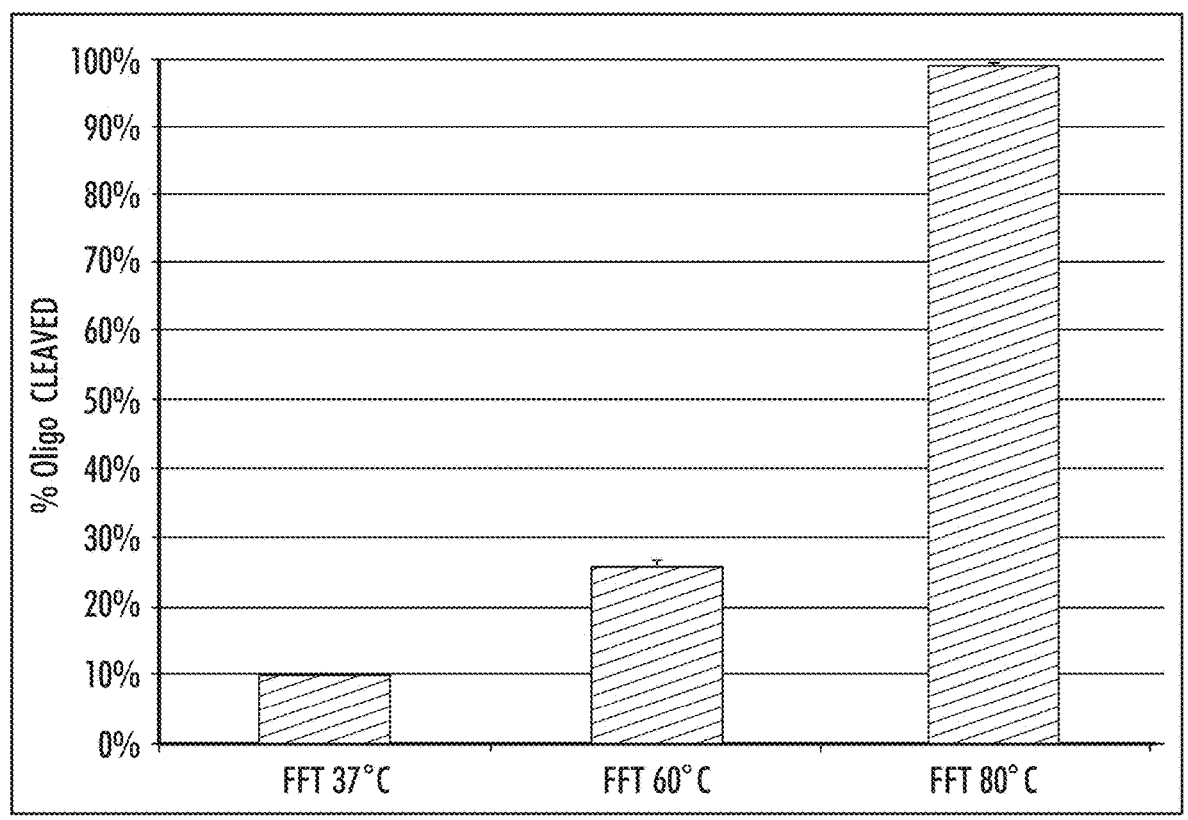
FIG. 10 graphically illustrates a temperature dependency of a retro Diels-Alder reaction (and release of a fluorescent si-RNA) for a furan-based linker product (connected to a nanoparticle) after 1 hour of heating at 37° C., 60° C., and 80° C.
Figure 11:
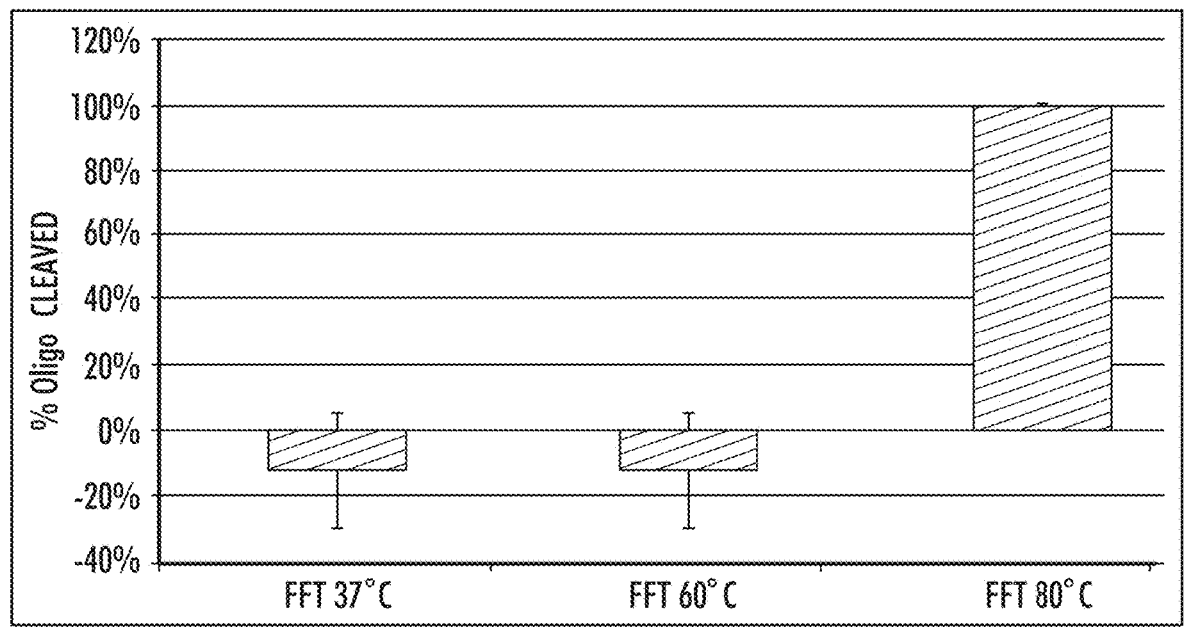
FIG. 11 graphically illustrates a temperature dependency of a retro Diels-Alder reaction (and release of the fluorescent si-RNA) for a thiophene-based linker product (connected to a nanoparticle) after 2 hours of heating at 37° C., 60° C., and 80° C.
Figure 12:
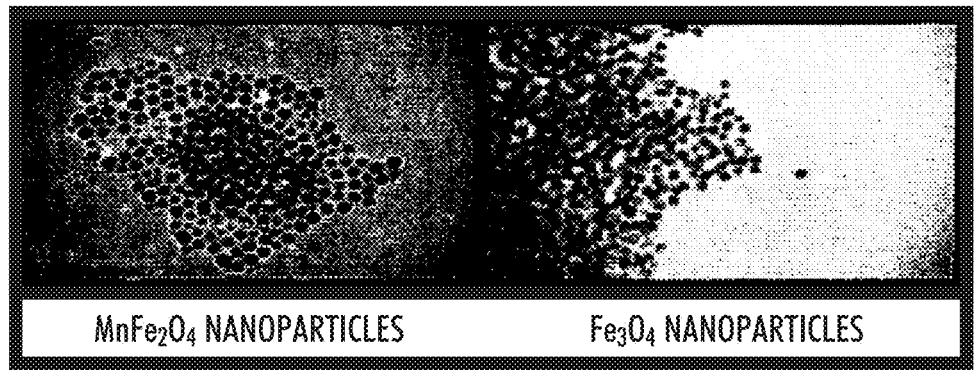
FIG. 12 illustrates transmission electron microscope (TEM) images of $MnFe_2O_4$ and $Fe_3O_4$ nanoparticles.
Figure 13:
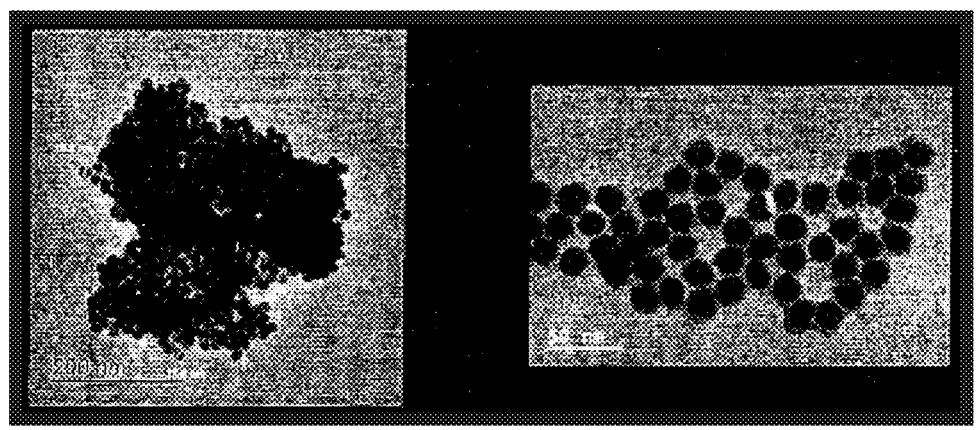
FIG. 13 illustrates TEM images of $CoFe_2O_4$ nanoparticles.
Figure 14:
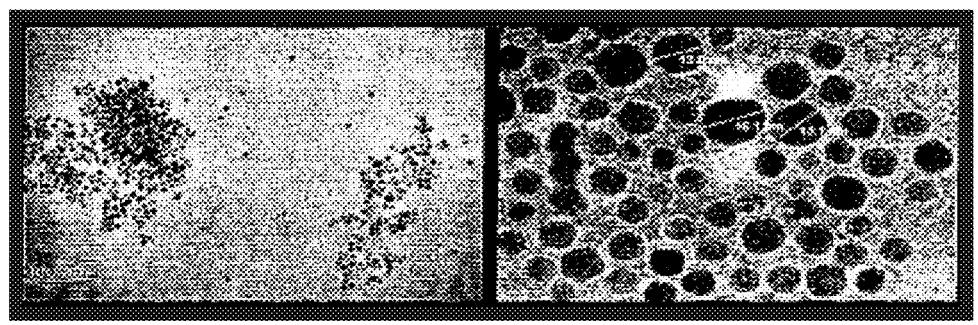
FIG. 14 illustrates TEM images of $NiFe_2O_4$ Nanoparticles.
Figure 15:
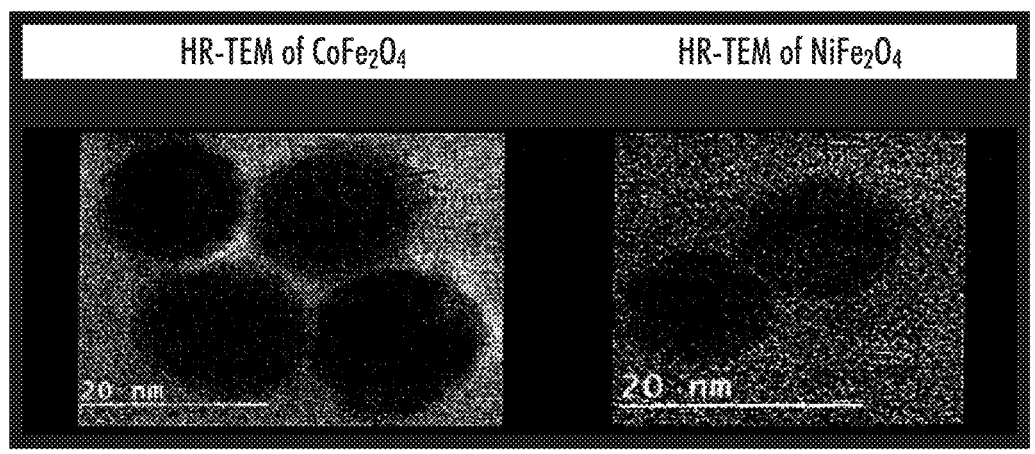
FIG. 15 illustrates high resolution TEM (HRTEM) images of $CoFe_2O_4$ and $NiFe_2O_4$ nanoparticles.

For different Diels-Alder cyclo-addition products, the retro (or reverse) Diels-Alder reaction will occur or be initiated at different temperatures (i.e., different activation temperatures). Thus, by varying the Diels-Alder cyclo-addition product in the linker group, breaking up or cleaving of the Diels-Alder cyclo-addition product (and concomitant decoupling of the therapeutic species and the nanoparticle) can be "tuned" to occur at different temperatures. For example, the activation temperature of the pyrrole-based linker group in FIG. 7 was measured and found to be 40° C., the furan-based linker group was measured and found to be 60° C., and the activation temperature of the thiophene-based linker group in FIG. 7 was found to be around 80° C. It was also found that cleavage of a furan-based linker occurs faster at lower temperatures than the thiophene-based linker, as seen for example in FIGS. 10 and 11. FIG. 10 shows temperature dependency of a retro Diels-Alder reaction (and release of a fluorescent si-RNA) for the furan-based linker group (connected to a nanoparticle) after 1 hour of heating at 37° C., 60° C., and 80° C., where 25% cleavage of the linker is observed at 60° C. FIG. 11 shows temperature dependency of a retro Diels-Alder reaction (and release of the fluorescent si-RNA) for a thiophene-based linker group (connected to a nanoparticle) after 2 hours of heating at 37° C., 60° C., and 80° C., where cleavage of the linker is not observed until 80° C.

In some embodiments, the activation temperature of the retro (or reverse) Diels-Alder reaction of a linker described herein is between 30° C. and 170° C., between 30° C. and 150° C., between 40° C. and 85° C., between 45° C. and 100° C., between 50° C. and 80° C., or between 55° C. and 70° C.

As described further herein, the activation temperature of a retro Diels-Alder reaction can be reached, at least in part, by transfer of thermal energy from the nanoparticle to the linker, raising the temperature of the linker or of the immediate environment of the linker.

Additionally, in some embodiments, compositions described herein can include two or more different linkers, wherein the linkers comprise different Diels-Alder cycloaddition products. The use of a plurality of differing linkers can allow for decoupling of therapeutic species and nanoparticles at different temperatures. In this manner, the amount and/or type of therapeutic species delivered to a biological compartment can be controlled. For example, if different therapeutic species are attached to different nanoparticles via different linkers, then the release of the different therapeutic species can be controlled by heating the population of different nanoparticles to the retro (or reverse) Diels-Alder activation temperature of one linker group, but not the other. Such heating can result in release of one therapeutic species, but not the other.

A linker described herein can be connected, attached, or bonded to a therapeutic species and/or nanoparticle in any manner not inconsistent with the objectives of this disclosure. For example, in some cases, a linker is bonded to a nanoparticle via one or more metal-ligand bonds (such as shown in FIGS. 4-6 (for a metal nanoparticle) and for magnetic nanoparticles (not shown)). Such bonds can be covalent or non-covalent. For instance, in some embodiments, a linker is attached to a nanoparticle via one or more ionic bonds.

II. Methods of Delivering a Therapeutic and/or Diagnostic Species to an Environment In another aspect, methods of delivering a therapeutic and/or diagnostic species to an environment are described herein. In some instances, such a method comprises disposing a composition described herein in an environment, such as a biological compartment. Any composition described hereinabove in Section I can be used. For example, in some cases, the composition comprises a metal or magnetic nanoparticle and a linker joining the nanoparticle to the therapeutic species, wherein the linker comprises a Diels-Alder cyclo-addition product. A method described herein can further comprise initiating a retro Diels-Alder reaction to decompose the Diels-Alder cyclo-addition product of the composition. In this manner, the linker can be severed and the therapeutic species can be decoupled from the nanoparticle, including in a desired location.

Specific steps of methods described herein will now be described in further detail.

A. Disposing a Composition in an Environment

A composition described herein can be disposed in an environment in any manner not inconsistent with the objectives of this disclosure. Moreover, the environment can be any environment not inconsistent with the objectives of this disclosure. In some cases, for example, the environment is a biological environment or compartment. Such an environment or compartment, in some instances, comprises or consists essentially of a cell, tissue, organ, or body cavity of a living mammal, such as a human. Further, in some embodiments, a composition described herein is disposed in a biological compartment by injecting the composition into the compartment directly or indirectly, such as can be achieved by subcutaneous injection or injection into vasculature of a mammal. A composition described herein can also be disposed in a biological compartment of a mammal by topical application of the composition to a surface of skin or other surface of the mammal. In some cases, a composition described herein is disposed in a biological compartment by diffusion of the composition into the compartment, or by oral ingestion. Other methods of disposing a composition in an environment can also be used.

B. Initiating a Retro Diels-Alder Reaction

The step of initiating a retro Diels-Alder reaction to decompose the Diels-Alder cycloaddition product, thereby severing the linker and decoupling the therapeutic species from the magnetic or thermal-activated nanoparticle, can be performed or carried out in any manner not inconsistent with the objectives of this disclosure. Severing the linker and decoupling the therapeutic species releases the therapeutic species. In some embodiments when the linker is severed in a biological compartment, the therapeutic species is released into the biological compartment. In some embodiments, the step of initiating a retro Diels-Alder reaction comprises heating the nanoparticle of a composition described herein to an activation temperature of the retro Diels-Alder reaction.

As described above, heating the nanoparticle can be achieved in a different manner based on the type of nanoparticle (e.g., metal nanoparticle or magnetic nanoparticle). For a metal nanoparticle, for instance, heating can be achieved by irradiating the nanoparticle with light comprising a wavelength (or frequency) that matches or corresponds to a resonant frequency of the nanoparticle. Irradiating a nanoparticle with such light can result in the formation of resonant plasmons. These resonant plasmons can decay into phonons, which heat the particle, as described above.

In such embodiments wherein a metal nanoparticle is used, the applied light can have an average wavelength in the visible, infrared, or near infrared spectrums, as previously described above. Such wavelengths can be especially advantageous, in some cases, when used in sub-toxic intensities.

For magnetic nanoparticles, heating can be achieved by application of an alternating magnetic field. As described above, this magnetic energy can be converted to thermal energy, which heats the magnetic particles. In some such embodiments, the applied alternating magnetic field can have a frequency ranging from 100 to 1,000 kHz, 150 to 950 kHz, 200 to 900 kHz, 250 to 850 kHz, 300 to 800 kHz, 350 to 750 kHz, 400 to 700 kHz, 450 to 650 kHz, or 500 to 600 kHz. Not intending to be bound by theory, it is believed that these alternating magnetic field frequencies are sub-toxic.

One observed benefit of using an alternating magnetic field to heat magnetic nanoparticles, compared to irradiating plasmonic metal nanoparticles with light that matches a resonant frequency of at least one of the nanoparticles is the ability to heat the nanoparticles at greater depths in a biological compartment. Without wishing to be bound by any particular theory, this result is believed to occur because the alternating magnetic field is not attenuated to the same degree as light is by the biological compartment (due to the presence of water or one or more biomolecules). Thus, in some cases, compositions and methods described herein can be particularly suitable for use in deep-tissue cancer imaging and/or therapy.

III. Methods of Inducing Tissue Regeneration

In another aspect, methods of inducing tissue regeneration are described herein. In some instances, such a method comprises disposing a composition described herein in an environment, such as a biological compartment, and decomposing the Diels-Alder cycloaddition product, thereby severing the linker and decoupling the therapeutic species, as previously described in Section II. Any nanoparticle and linker described hereinabove in Section I can be used. In some embodiments, the therapeutic species comprises a tissue regenerative species, such as an osteogenic modulator, a chondrogenic modulator, an endotheliologenic modulator, or a myogenic modulator. Exemplary embodiments of tissue regenerative species comprise a nucleic acid, a microRNA ("miRNA"), a small interfering RNA (siRNA), a peptide, a small molecule, an antibiotic, an antifungal, an antibody, a protein, or any combination thereof. Specific embodiments of an osteogenic modulator, a chondrogenic modulator, an endotheliologenic modulator, a myogenic modulator can comprise one or more of the examples described in Section I herein.

In one embodiment, the tissue regenerative species is a miRNA-148b mimic. MiRN-148b induces differentiation of human autologous adipose derived mesenchymal stromal/stem cells (hASCs) into an osteogenic linage. In some instances, release of miRNA-148b into the biological compartment of a cell (such as hASCs) increases alkaline phosphatase (ALP) activity in the cell membranes and calcification (mineralization) of the cell. ALP is one of the early protein enzymes expressed during osteogenesis and is displayed on the extracellular portion of the plasma membrane, resulting in increased local concentration of inorganic phosphate, a mineralization promoter, and decreased concentration of extracellular pyrophosphate, an inhibitor of mineral formation. In some instances, release of miRN-148b using the methods described herein, induces upregulation in the expression of mRNA for early, middle, and late stage osteogenic marks, such as ALP, RunX2, osteocalcin (OCN).

IV. Methods of Treating Cancer

In another aspect, methods of treating cancer are described herein. In some instances, the method comprises disposing a composition described herein in an environment, such as a biological compartment, and decomposing the Diels-Alder cycloaddition product, thereby severing the linker and decoupling the therapeutic species, as previously described in Section II. Any nanoparticle and linker described hereinabove in Section I can be used. In some embodiments, the therapeutic species comprises an anti-cancer species according to any of the embodiments described in Section I herein.

In one embodiment, the anti-cancer species is a miRN-148b mimic. miRN-148b has been shown to act as a tumor suppressor and promote carcinogenesis. While not intending to be bound by any theory, it is believed that miRN-148b acts as a tumor suppressor by targeting specific oncogenes in a wide variety of tissues, dramatically suppressing the growth of cancer cells, attributable to induction of apoptosis and cell-cycle arrest at S-phase. In some instances, release of miRN-148b using the methods described herein, treats cancers by suppressing the growth of cancer cells, or killing cancer cells.

Additional aspects of compositions and methods of this disclosure are further illustrated in the following non-limiting examples.

Example 1

Synthesis of Silver Nanoparticles

Colloidal silver nanoparticles (SNPs) were prepared as follows, yielding SNPs of approximately 75 nm in diameter size. At room temperature, 35 mL of each 125 mM silver nitrate ($AgNO_3$) and 61.5 mM formaldehyde (HCOH) were incrementally added 0.5 mL/min into a pre-made solution of 0.5 g NaOH, 0.31 g HPC, 330 mL deionized (DI) water (18.2 MX), and 5 mL Antifoam A. For purification, the nanoparticles were filtered via dialysis and freeze-dried under vacuum for 72 h before use. A stock solution of 200 ppm in DI water was later prepared for further chemical modification.

Example 2

Synthesis of Magnetically-Activated Nanoparticles

Magnetically-activated $AuFe_3O_4$ dumbbell nanoparticles were synthesized as described in, Yu, Heng, et al. "Dumbbell-like Bifunctional Au—$Fe_3O_4$ Nanoparticles." *Nano Letters* 5.2 (2005): 379-82, which is incorporated by reference in its entirety herein. Under nitrogen flow, 0.30 ml $Fe(CO)_5$ (2 mmol) was injected into a pre-mixed solution consisting of 1.87 mL oleic acid (6 mmol), 1.97 mL oleylamine (6 mmol), 2.58 g 1,2-hexadecandiol (10 mmol) and 20 ml 1-octadecene at 120° C. for 20 min. After 3 min, 40 mg of $HAuCl_4.(H_2O)_3$ (0.1 mmol), 0.5 ml oleylamine (1.5 mmol) and 5 ml 1-octadecene were added to the solution. The mixture was then heated to ~300° C. by reflux for 45 min, cooled to room temperature, and aerated for an hour. The particles were precipitated out with either iso-propanol or ethanol and a magnet bar, washed, and re-dispersed in hexane. FIGS. 12-15 show TEM images of $MnFe_2O_4$ and $Fe_3O_4$ nanoparticles (FIG. 12), $CoFe_2O_4$ nanoparticles (FIG. 13), $NiFe_2O_4$ nanoparticles (FIG. 14), and $CoFe_2O_4$ and $NiFe_2O_4$ nanoparticles (FIG. 15, HRTEM images) made in accordance with this procedure.

Example 3

Formation of Diels-Alder Linker

Figures 8, 9:
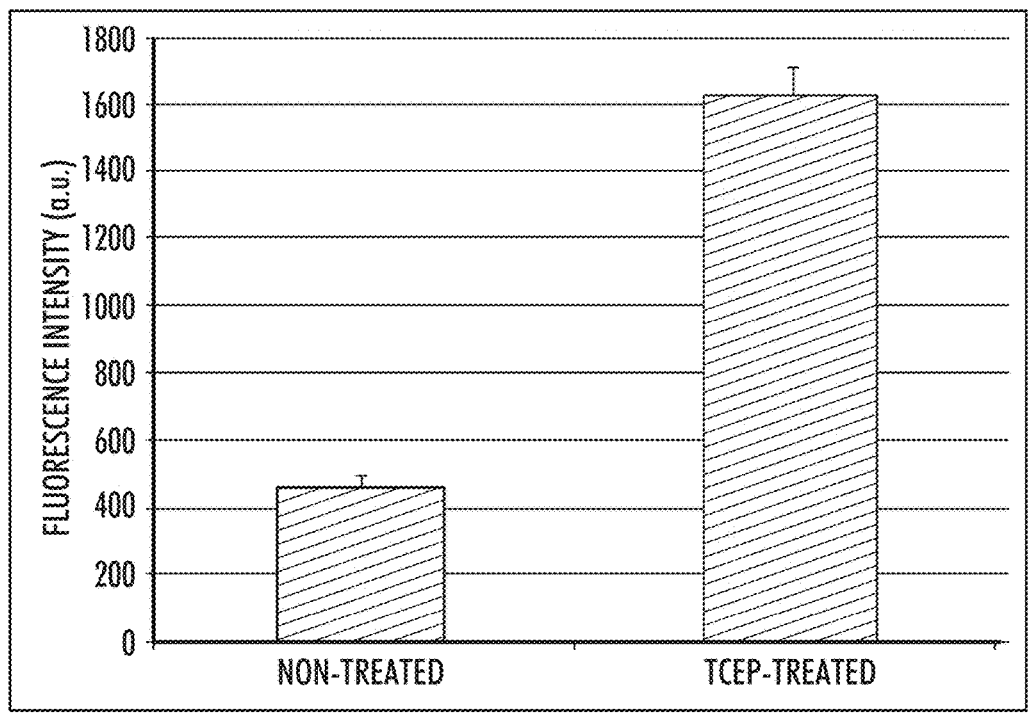
FIG. 8 displays the calculated forward and reverse $\Delta H_{rxn}$ for formation of three different linkers.
FIG. 9 shows fluorescence intensity of a control (non-treated) sample and a chemically cleaved (treated) sample including a product formed by reacting the furan-based linker with EDC/NHS and a fluorescently-labeled si-RNA.

Three different linkers comprising a Diels Alder cycloaddition product were formed by the reaction shown in FIG. 5, where X is O (furan), S (thiophene), or NH (pyyrole). FIG. 8 includes the calculated forward and reverse $\Delta H_{rxn}$ for formation of the three different linkers by the (forward) Diels-Alder reaction in FIG. 5 and reverse (retro) Diels-Alder reaction in FIG. 6. The Diels-Alder cycloaddition product of the linker can be chosen, as was done here, such that the forward cycloaddition reaction is more energetically favorable than the backward (retro or reverse) reaction. This allows for the Diels-Alder cycloaddition product to be formed at subcleavage (or retro or reverse Diels-Alder reaction) temperatures.

For the cycloaddition between 6-maleimidohexanoic acid and 2-furanmethanethiol, 4.18 g of the dienophile, the maleimide, was combined with 1 mL of the diene reagent, in a 1:1 (v/v) dichloromethane/methanol ("DCM:MeOH") solvent mixture. The reaction was allowed to proceed for 7 days under agitating conditions at room temperature in a sealed container. For the Diels-Alder reactions between the 2-thienylmethanethiol (0.5 mL) and the 6-maleimidohexanoic acid (2.11 g); and the pyrrole-2-carboxylic acid (0.555 g) and 6-maleimidohexanoic acid (2.11 g), the reagents were again mixed together in MeOH-only solvent. Both the reactions for the pyrrole and thiophene were carried out in an oil bath at 60° C. for 3 days under controlled ventilation. The bicyclic products between the different dienes and dienophile were purified by HPLC and characterized via MALDI-MS, $^1$H and $^{13}$C NMR.

MALDI, FTIR, $^1$H NMR, and $^{13}$C NMR confirm synthesis of all three linkers comprising pyrrole, furan, and thiophene cycloaddition product. Results for the linker comprising the furan cycloaddition product, the thiophene cycloaddition product and the pyrrole cycloaddition product are presented in Table 1 below. The $^{13}$C NMR peaks, the FTIR major peaks, and the M/Z ratio from the MALDI data all indicate formation of the respective linkers. The M/Z ratio (found) from the MALDI data indicates a product of the expected m/z ratio (calculated) in positive ion mode of the respective linkers.

TABLE 1

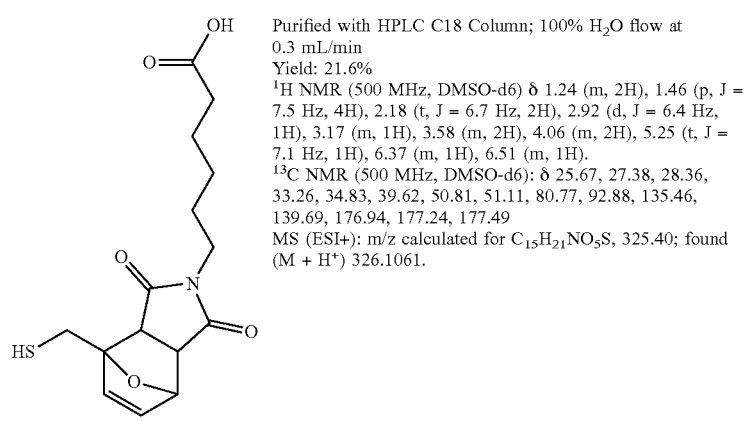

Purified with HPLC C18 Column; 100% $H_2O$ flow at 0.3 mL/min
Yield: 21.6%
$^1$H NMR (500 MHz, DMSO-d6) δ 1.24 (m, 2H), 1.46 (p, J = 7.5 Hz, 4H), 2.18 (t, J = 6.7 Hz, 2H), 2.92 (d, J = 6.4 Hz, 1H), 3.17 (m, 1H), 3.58 (m, 2H), 4.06 (m, 2H), 5.25 (t, J = 7.1 Hz, 1H), 6.37 (m, 1H), 6.51 (m, 1H).
$^{13}$C NMR (500 MHz, DMSO-d6): δ 25.67, 27.38, 28.36, 33.26, 34.83, 39.62, 50.81, 51.11, 80.77, 92.88, 135.46, 139.69, 176.94, 177.24, 177.49
MS (ESI+): m/z calculated for $C_{15}H_{21}NO_5S$, 325.40; found (M + H$^+$) 326.1061.

Furan Diels-Alder linker

TABLE 1-continued

| | |
|---|---|
| 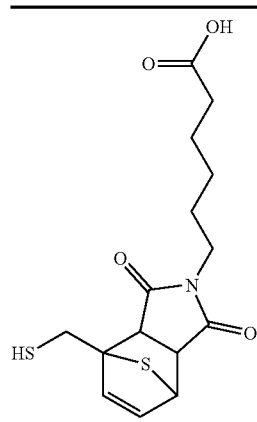<br>Thiophene Diels-Alder linker | Purified with HPLC C18 Column; 1.3% ACN 98.7% $H_2O$ flow at 0.3 ml/minute<br>Yield: 24.8%<br>$^1$H NMR (500 MHz, DMSO-d6) δ 1.20 (m, 2H), 1.46 (m, 4H), 2.17 (t, J = 7.8 Hz, 2H), 2.64 (dd, J = 19.9, 4.3 Hz, 1H), 3.10 (dd, J = 20.1, 9.5 Hz, 1H), 3.31 (m, 2H), 3.42 (dd, J = 12.6, 7.36 Hz, 2H), 3.87 (dd, J = 9.5, 4.4 Hz, 1H), 6.74 (m, 1H), 6.91 (m, 1H).<br>$^{13}$C NMR (500 MHz, DMSO-d6): δ 24.49, 26.15, 27.21, 33.50, 35.69, 39.42, 47.71, 51.21, 51.68, 52.58, 134.89, 140.64, 175.54, 175.55, 177.02<br>MS (ESI+): m/z calculated for $C_{15}H_{21}NO_4S_2$, 341.44; found (M + H$^+$) 342.08. |
| 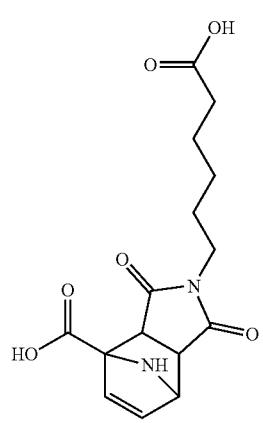<br>Pyrrole Diels-Alder linker | Purified with HPLC C18 Column; 20% ACN and 80% $H_2O$ flow at 0.3 ml/minute.<br>Yield: 23.8%<br>$^1$H NMR (500 MHz, DMSO-d6) δ 1.22 (m, 2H), 1.55 (m, 4H), 2.18 (t, J = 7.4 Hz, 2H), 3.01 (m, 1H), 3.59 (m, 2H), 5.90 (dt, J = 17.7, 5.8 Hz, 1H), 6.13 (q, J = 2.7 Hz, 1H), 6.68 (m, 1H), 7.01 (m, 1H).<br>$^{13}$C NMR (500 MHz, DMSO-d6) δ 24.45, 26.10, 27.20, 33.92, 38.43, 44.11, 51.67, 55.82, 56.11, 123.83, 134.93, 162.35, 171.57, 176.14, 177.25.<br>MS (ESI+): m/z calculated for $C_{15}H_{18}N_2O$, 322.23; found (M + H$^+$): 323.16. |

Example 4

Connection of Nanoparticle to Linker

For nanoparticle attachment to any one of the linkers described in Example 3, the solutions described in Examples 1 and 2 were dried with nitrogen gas to remove excess solvent and concentrate the samples prior to suspension, without HPLC purification. Additionally, in the case of the pyrrole-2-carboxylic acid Diels-Alder reaction, the diene was first cross-linked with cystamine using EDC coupling chemistry for SNP modification. Briefly, EDC (1-Ethyl-3-(3-dimethylaminopropyl)-carbodiimide) (0.500 g), NHS (N-hydroxysuccinimide) (0.800 g) and cystamine (0.400 g) were added to the pyrrole-2-carboxylic acid (0.555 g) and agitated overnight at room temperature.

Three 1 mL-aliquoted SNPs was centrifuged (10,000 rpm, 15 min) and after removal of the supernatant, 0.5 mL of each Diels-Alder product was added directly to one of the 1 mL aliquots of the pelleted SNPs. The SNP surface modification step was left to proceed at room temperature for 24 h for all the three generated products. The nanoparticles were then washed three times by centrifuging for 10 min at 10,000 rpm consecutively, in which each step involved removal of the supernatant and resuspension in 1 mL of 70% (v/v) ethanol.

Example 5

Connection of Nanoparticle/Linker with Fluorescent-Labeled Small Interfering RNA (Si-RNA)

The above-described three linkers (pyrrole, furan, and thiophene-based) were respectively reacted with EDC/NHS (N-ethyl-N'-(3-(dimethylamino)propyl)carbodiimide/N-hydroxysuccinimide) and a fluorescently-labeled si-RNA. In this embodiment, a 3'amine/5'-FAM modified anti-sense RFP single stranded siRNA was used having a sequence of UUGGAGCCGUACUGGAACUUG ("miRN-148b").

Specifically, to conjugate a FAM-tagged RFP antisense siRNA mimic, an EDC coupling protocol was used with 100 mL of an aqueous EDC/NHS (100 mM) stock solution added to each of the three resuspended nanoparticle aliquots prepared in Example 3, followed by 50 mL of the amine-terminated siRNA (4 mM). After 24 h, the particles were again centrifuged, washed, and resuspended in DI water. A control sample in which cystamine modified SNPs were linked to the 6-maleimidohexanoic acid via EDC coupling was also prepared, similarly to the pyrrole-based reaction described above, but without addition of the diene, to test the stability of both the amide and thiol linkages. Conjugation of the linkers and siRNA was tested by chemically reducing the Ag-linker bond using TCEP reagent (tris(2-carboxyethyl) phosphine hydrochloride) and measuring FAM intensity of the supernatant.

The products of these reactions (pyrrole, furan, and thiophene-based) were analyzed. For example, the temperature dependency of the retro Diels Alder reaction (and release of the fluorescent si-RNA) was evaluated. FIG. 9 shows fluorescence intensity of a control (non-treated) sample and a chemically cleaved (treated) sample including a product formed by reacting the furan-based linker with EDC/NHS and a fluorescently-labeled si-RNA. The fluorescence intensity of the treated sample is assumed to indicate maximum release (due to cleavage/retro (or reverse) Diels Alder reaction).

Figure 16:
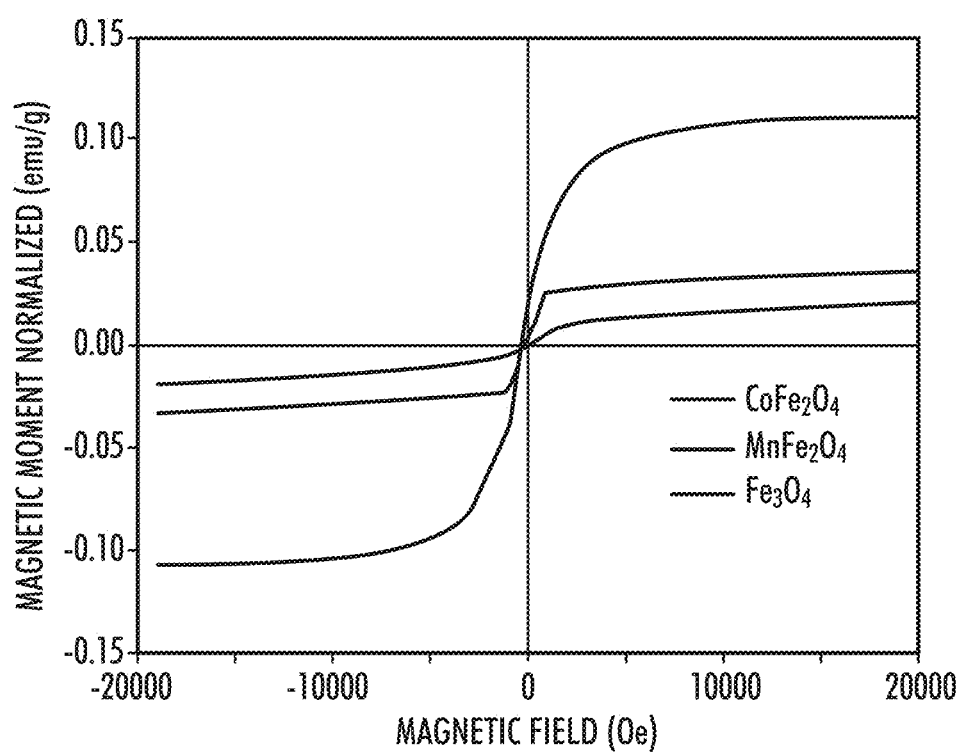
FIG. 16 graphically illustrates Hysteresis Loops of $CoFe_2O_4$, $MnFe_2O_4$ and $Fe_3O_4$ nanoparticles.
Figure 17:
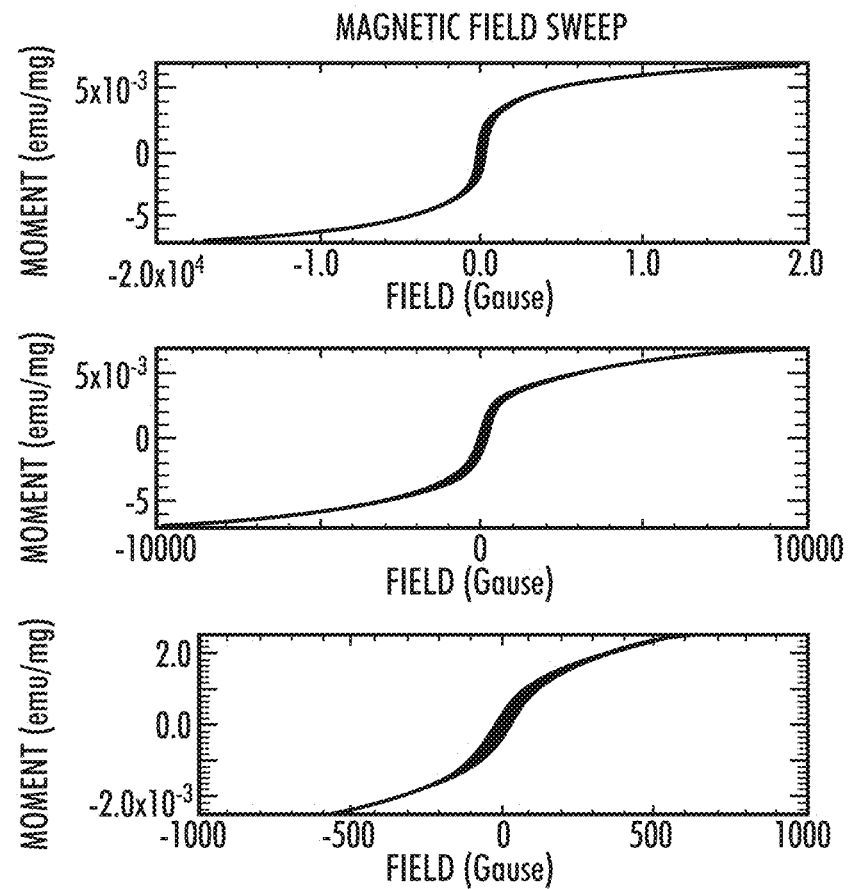
FIG. 17 graphically illustrates a magnetic field sweep.

The magnetic moment of three different nanoparticles used were also measured. FIG. 16 shows hysteresis loops for each of these nanoparticles, and FIG. 17 shows a magnetic field sweep. Specifically for FIG. 16, the curve with smallest vertical change in y-direction is the $MnFe_2O_4$, the curve with the largest vertical change is the $CoFe_2O_4$, and the middle curve is $Fe_2O_4$.

Figure 18:
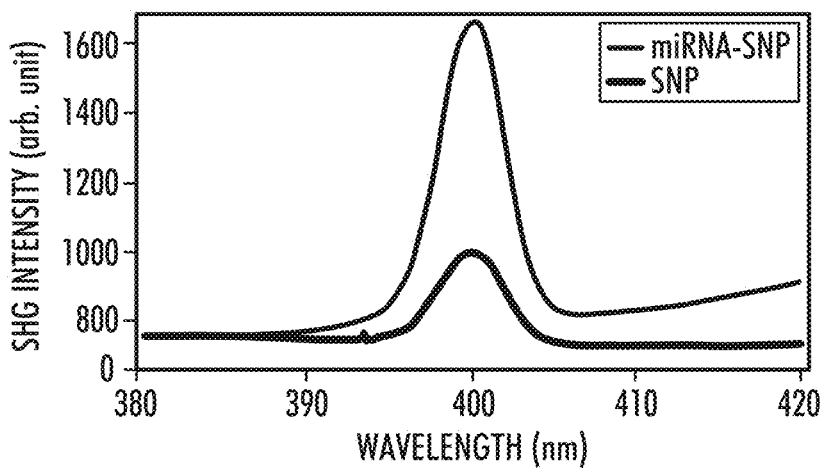
FIG. 18 graphically illustrates second harmonic intensity of a thiophene, furan, or pyrrole-based linker connecting an si-RNA to a plasmonic silver nanoparticle (SNP).
Figure 19:
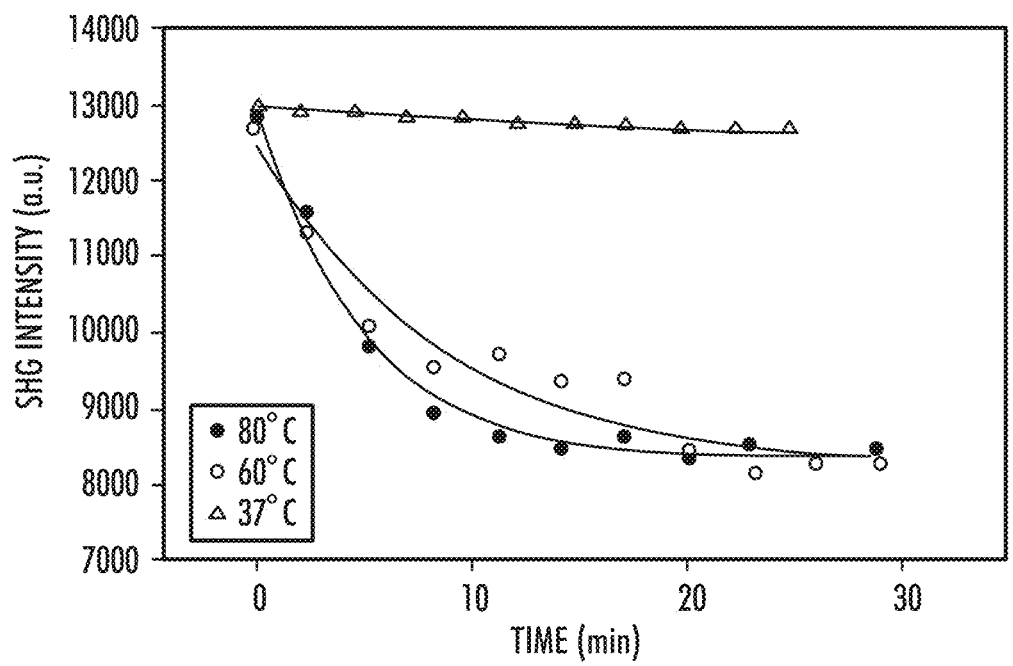
FIG. 19 graphically illustrates second harmonic intensity at particular temperatures as a function of time for a composition comprising a siRNA-SNP with a pyrrole-based linker.

FIG. 18 graphically illustrates second harmonic intensity of a thiophene, furan, or pyrrole-based linker connecting an si-RNA to a plasmonic silver nanoparticle (SNP). FIG. 19 shows second harmonic (SHG) intensity, at particular temperatures, as a function of time for a composition comprising a siRNA-SNP with the pyrrole-based linker described herein in the Examples. Decreasing second harmonic intensity is indicative of cleaved via a retro (or reverse) Diels-Alder reaction, disconnecting or releasing SNP from siRNA.

Figure 20:
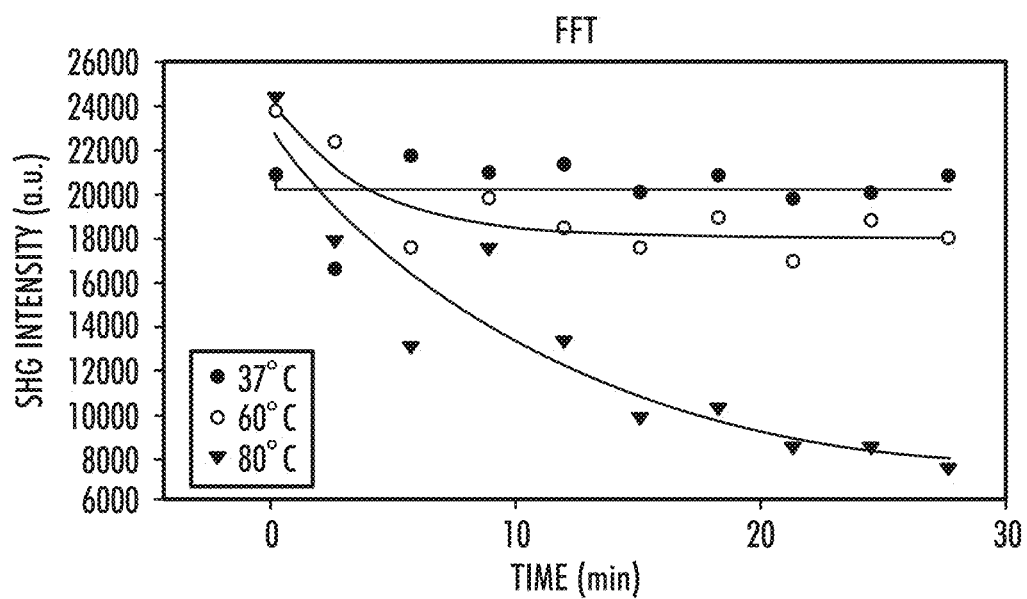
FIG. 20 graphically illustrates second harmonic intensity at particular temperatures as a function of time for a composition comprising a plasmonic silver nanoparticle connected to si-RNA via a furan-based linker.

FIG. 20 shows second harmonic (SHG) intensity, at particular temperatures, as a function of time for a composition comprising a plasmonic silver nanoparticle connected to siRNA via the furan-based linker described herein in the Examples.

Figure 21:
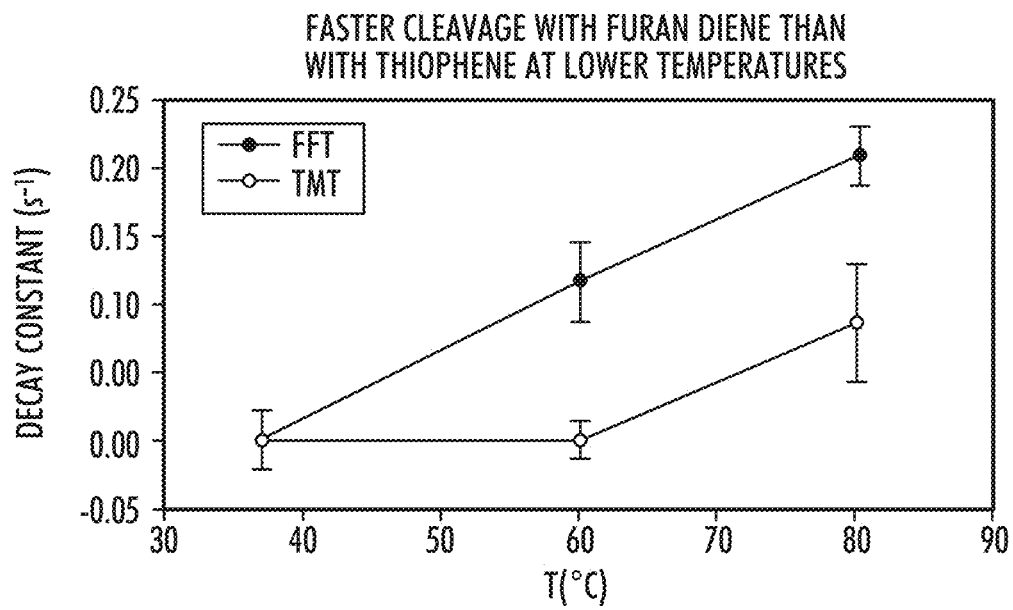
FIG. 21 graphically compares decay constants for a composition with a furan-based linker (FFT) to a composition with a thiophene-based linker (TMT).

Decay constants of compositions comprising a plasmonic silver nanoparticle connected to siRNA via the furan-based and thiophene-based linkers described herein in the Examples were measured and compared. FIG. 21 shows that decay constant for the composition comprising the furan-based linker was significantly higher than that for the composition comprising the thiophene-based linker at 60° C. and at 80° C.

Figure 22:
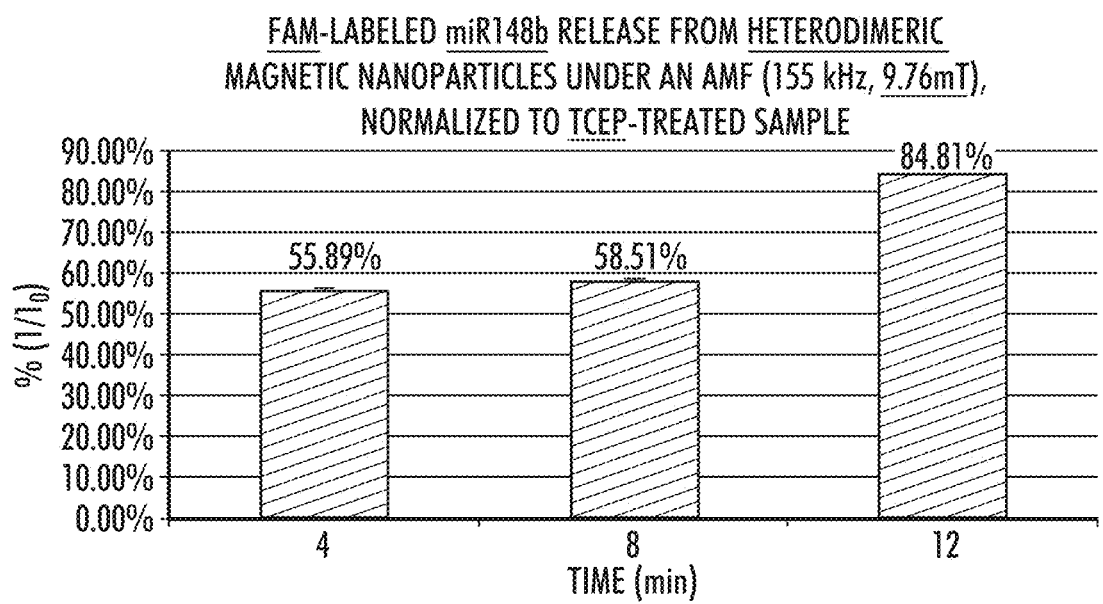
FIG. 22 graphically illustrates relative release of the fluorescently labeled miRNA from the heterodimeric $Fe_3O_4$/Au was measured with respect to time at 155 kHz and 9.76 mT.

Compositions comprising heterodimeric $Fe_3O_4$/Au magnetic nanoparticles connected to fluorescently labeled microRNA (miRNA) were also formed. Relative release of the fluorescently labeled miRNA from the heterodimeric $Fe_3O_4$/Au was measured with respect to time at 155 kHz and 9.76 mT, normalized to a chemically released sample that was assumed to be near total release, as seen for example in FIG. 22.

Example 6

Anti-Cancer Effects of miRN-148b Released from Retro Diels-Alder Reaction in PAM2 Cells The anti-cancer effects towards PAM2 skin cancer cells of miRN-148b released from compositions described herein were explored using a furan-based linker conjugated with a FAM-tagged miRN-148b and an SNP. The furan-based linker composition was prepared according to Examples 1-5. SNPs surface-modified with miRNA mimics via Diels-Alder linkage, were sterilized in 70/30% ethanol and water solution prior to washing and resuspension in RNAse-free water. Subsequently, appropriate nanoparticle solution volumes were added, based on required dosages, to the adherent monolayer PAM2 cells at optimal seeding densities, immersed in appropriate cell culture media. Transfection was allowed to occur at 37° C. for 24 h.

Figure 23A:
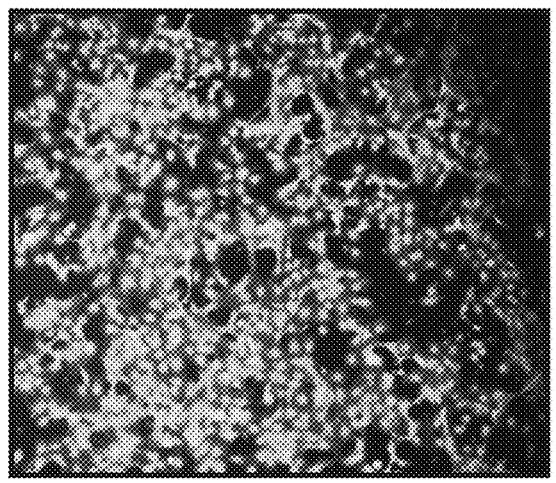
FIG. 23A is a negative control showing fluorescence of the PAM2 cells in the presence of silver nanoparticles.
Figure 23B:
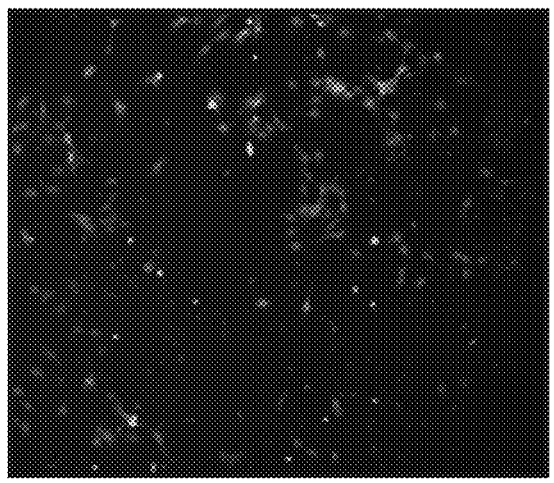
FIG. 23B is a positive control showing PAM2 cells transfected with FAM-tagged miRN-148b.
Figure 23C:
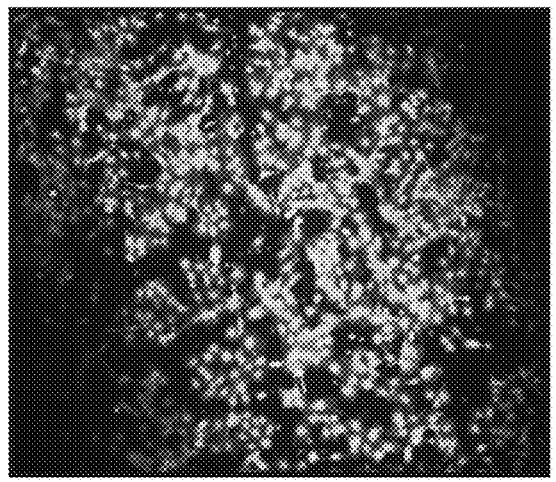
FIG. 23C shows PAM2 cells in the presence of a furan-based linker conjugated with a (fluorescein) FAM-tagged miRN-148b and an SNP, where the composition has not been light activated.
Figure 23D:
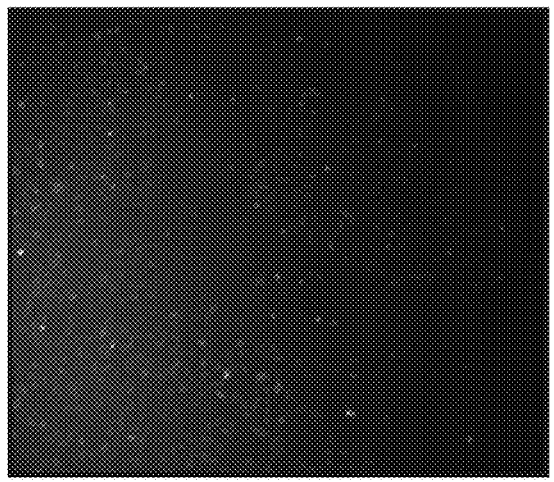
FIG. 23D shows PAM2 cells in the presence of a furan-based linker conjugated with a FAM-tagged miRN-148b and an SNP composition, where the composition has been light activated.

As seen in FIGS. 23A-23D, PAM2 cells were treated with the furan-based linker composition. FIG. 23A is a negative control showing fluorescence of the PAM2 cells in the presence of silver nanoparticles prepared in accordance with Example 1 after 7 days. FIG. 23B is a positive control showing PAM2 cells transfected with FAM-tagged miRN-148b 7 days after transfection. FIG. 23C shows PAM2 cells in the presence of a furan-based linker conjugated with a FAM-tagged miRN-148b and an SNP composition after 7 days, where the composition has not been light activated. FIG. 23D shows PAM2 cells in the presence of a furan-based linker conjugated with a FAM-tagged miRN-148b and an SNP composition after 7 days, where the composition has been light activated at 420 nm.

As seen in FIGS. 23B and 23D, the PAM2 cells displayed reduced cell proliferation and growth in the presence of the positive control (FIG. 23B) and the light activated composition (FIG. 23D). Particularly, cell proliferation and growth was most dramatically reduced in the presence of the light activated composition in FIG. 23D. Cell growth in the negative control (FIG. 23A) and the composition not light activated (FIG. 23C) displayed normal cell behavior. Thus, light or magnetic activated compositions described herein can in some instances release anti-cancer/tumor therapeutic agents in cells using a retro Diels-Alder mechanism, and the released therapeutic agents can display in vivo activity towards cancer cells.

Example 7

Anti-Cancer Effects of miRN-148b Released from Retro Diels-Alder Reaction in Ras-Induced Keratinocyte Cells The anti-cancer effects towards Ras-induced keratinocyte lung cancer cells of miRN-148b released from compositions described herein were explored using a furan-based linker conjugated with a FAM-tagged miRN-148b and an SNP. The furan-based linker composition was prepared according to Examples 1-5. SNPs surface-modified with miRNA mimics via Diels-Alder linkage, were sterilized in 70/30% ethanol and water solution prior to washing and resuspension in RNAse-free water. Subsequently, appropriate nanoparticle solution volumes were added, based on required dosages, to the adherent monolayer PAM2 cells at optimal seeding densities, immersed in appropriate cell culture media. Transfection was allowed to occur at 37° C. for 24 h.

Figure 24A:
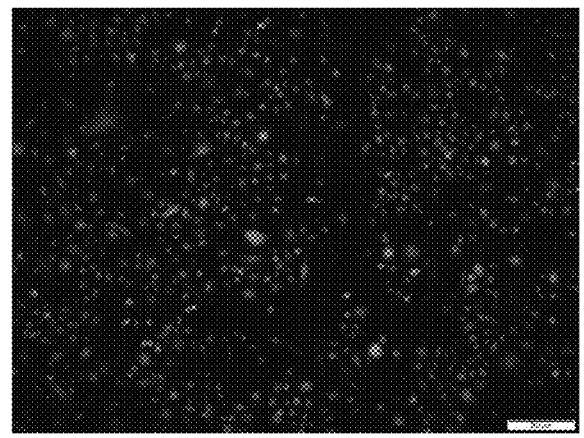
FIG. 24A is a negative control showing fluorescence of Ras-induced keratinocyte cells.
Figure 24B:
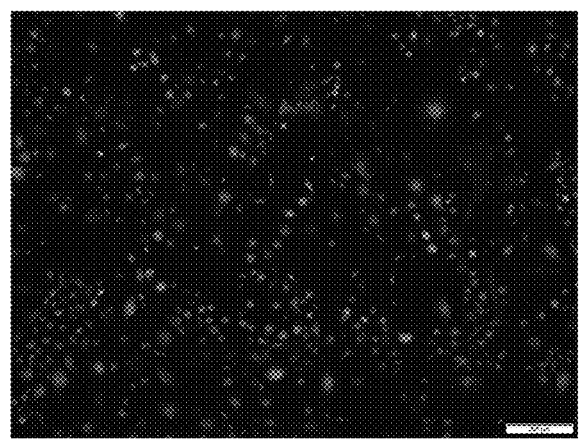
FIG. 24B is a positive control showing fluorescence of Ras-induced keratinocyte cells chemically transfected with 100 Nm miRN-148b.
Figure 24C:
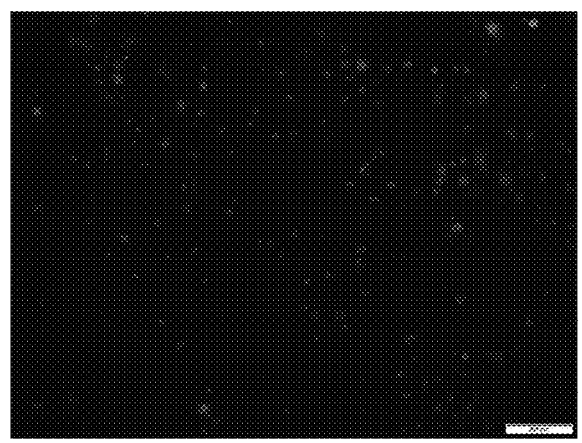
FIG. 24C shows fluorescence of Ras-induced Keratinocyte cells in the presence of a furan-based linker conjugated with a FAM-tagged miRN-148b and an SNP composition, where the composition has been light activated.

FIG. 24A is a negative control of keratinocyte cells in the absence of the composition and FAM-tagged miRN-148b after 7 days. FIG. 24B is a positive control of keratinocyte cells after 7 days, which have been transfected with FAM-tagged miRN-148b (100 nM). FIG. 24C shows keratinocyte cells that have been transfected with a composition comprising the furan-based linker conjugated with a FAM-tagged miRN-148b and an SNP, where the cells have been activated with light at 420 nm.

As seen in FIG. 24C, the keratinocyte cells displayed reduced cell proliferation and growth in the presence of light activated composition after 7 days. Cell growth in the negative control (FIG. 24A) and cells transfected with only FAM-tagged miRN-148b (FIG. 24B) displayed normal cell behavior. Thus, light or magnetic activated compositions described herein can in some instances release anti-cancer/tumor therapeutic agents in cells using a retro Diels-Alder mechanism, and the released therapeutic agents can display in vivo activity towards cancer cells.

Example 8

Tissue Regenerative Effects of miRN-148b Released from Retro Diels-Alder Reaction The tissue regenerative effects of miRN-148b released from compositions described herein were explored using a furan-based linker conjugated with a FAM-tagged miRN-148b and a magnetic nanoparticle. Specifically, the osteoinductive effects of miRN-148b on hASCs were explored using the furan-based linker composition prepared according to Examples 1-5. Magnetic nanoparticles surface-modified with miRNA mimics via Diels-Alder linkage, were sterilized in 70%/30% ethanol and water solution prior to washing and resuspension in RNAse-free water. Subsequently, appropriate nanoparticle solution volumes were added, based on required dosages, to the adherent monolayer hASCs cells at optimal seeding densities, immersed in appropriate cell culture media. Transfection was allowed to occur at 37° C. for 24 h.

Figure 25A:
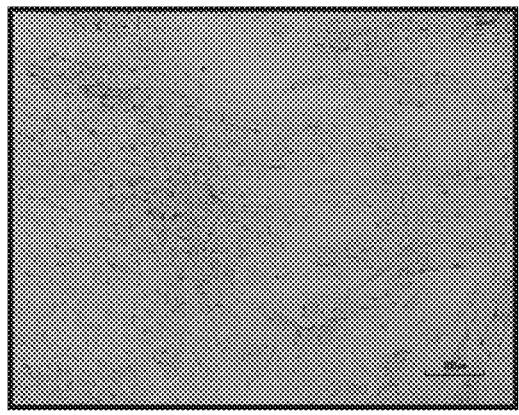
FIG. 25A shows a negative control of stromal media and Alizarin Red Staining D21 of hASCs cells.
Figure 25B:
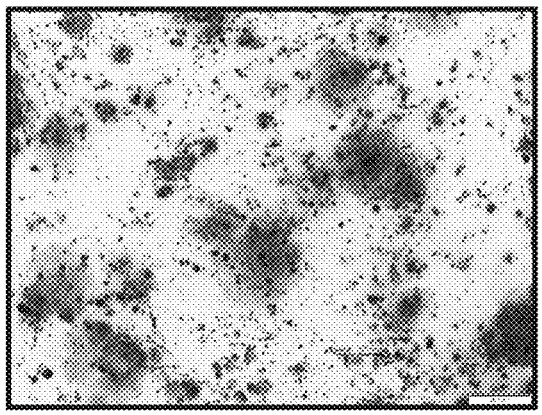
FIG. 25B shows a positive control of osteogenic media and Alizarin Red Staining D21 of hASCs cells.
Figure 25C:
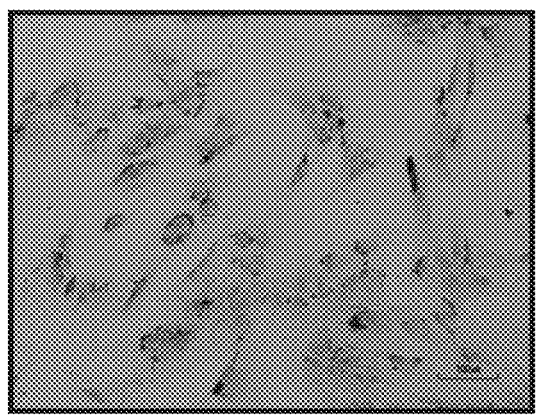
FIG. 25C shows a negative control of Alizarin Red Staining D21 of hASCs cells transfected with $AuFe_3O_4$ nanoparticles without RF activation.
Figure 25D:
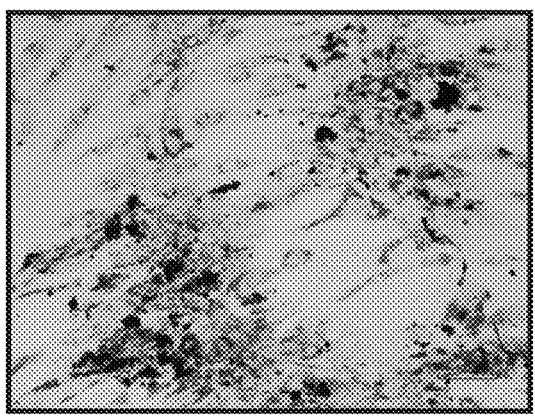
FIG. 25D shows an Alizarin Red Staining D21 of hASCs cells transfected with $AuFe_3O_4$ nanoparticles with miRN-148b attached with a furan-based Diels-Alder linker after RF activation.

FIG. 25A shows a negative control of stromal media and Alizarin Red Staining D21 of hASCs cells. FIG. 25B shows a positive control of osteogenic media and Alizarin Red Staining D21 of hASCs cells. FIG. 25C shows a negative control of Alizarin Red Staining D21 of hASCs cells transfected with AuFe$_3$O$_4$ nanoparticles without RF activation. FIG. 25D shows a Alizarin Red Staining D21 of hASCs cells transfected with AuFe$_3$O$_4$ nanoparticles with miRNA148b attached with a furan-based Diels-Alder linker after radio frequency (RF) activation.

As seen in FIG. 25A, hASCs cells grown on stromal media display very low levels of calcification, whereas hASCs cells grown on osteogenic media display high levels of calcification (FIG. 25B). In the presence of AuFe$_3$O$_4$ nanoparticles without a linker and therapeutic agent, the hASCs cells display low levels of calcification (FIG. 25C). However, hASCs cells that have been transfected with AuFe$_3$O$_4$ nanoparticles with miRN-148b attached with a furan-based Diels-Alder linker, display increased calcification after RF activation, showing that the composition releases miRN-148b upon RF activation, and the miRN-148b induces osteogenesis (FIG. 25D). Thus, light or magnetic activated compositions described herein can in some instances release tissue regenerative therapeutic agents in cells using a retro Diels-Alder mechanism, and the released therapeutic agents can display in vivo tissue regenerative activity in the cells.

Figure 26A:
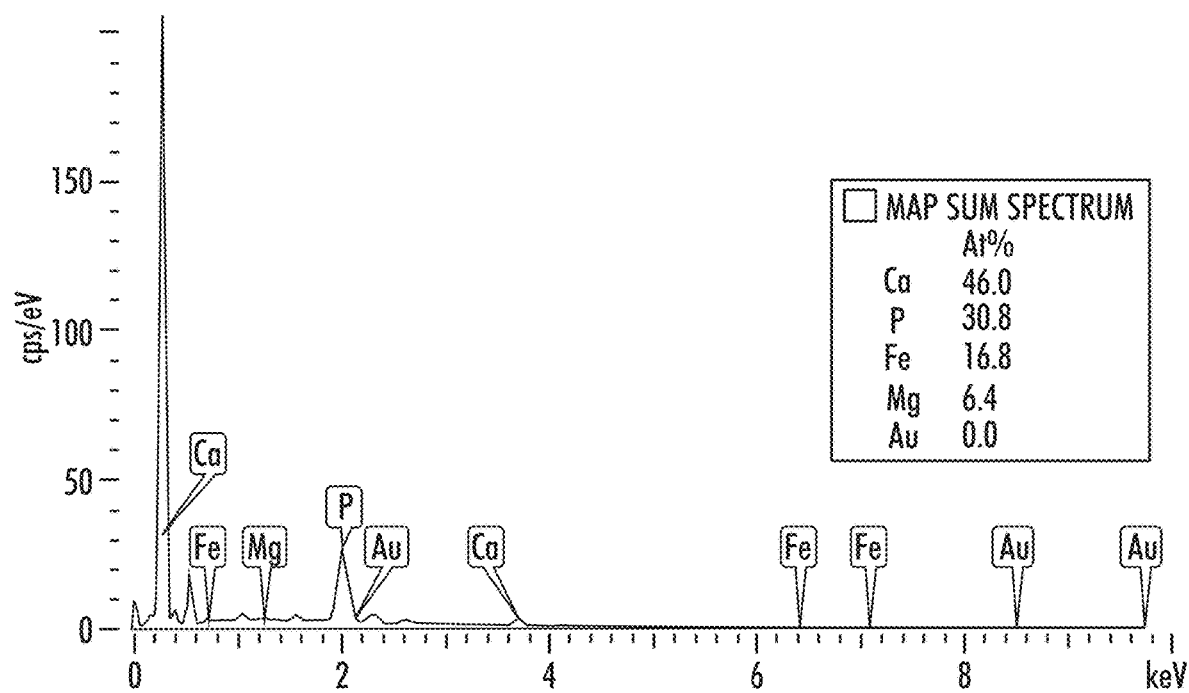
FIG. 26A is a graphical representation of SEM/EDS (scanning electron microscope/energy dispersive x-ray spectroscopy) showing mineralization levels of hASC cells with RF Activated AuFe3O4 nanoparticles without miRN-148b.
Figure 26B:
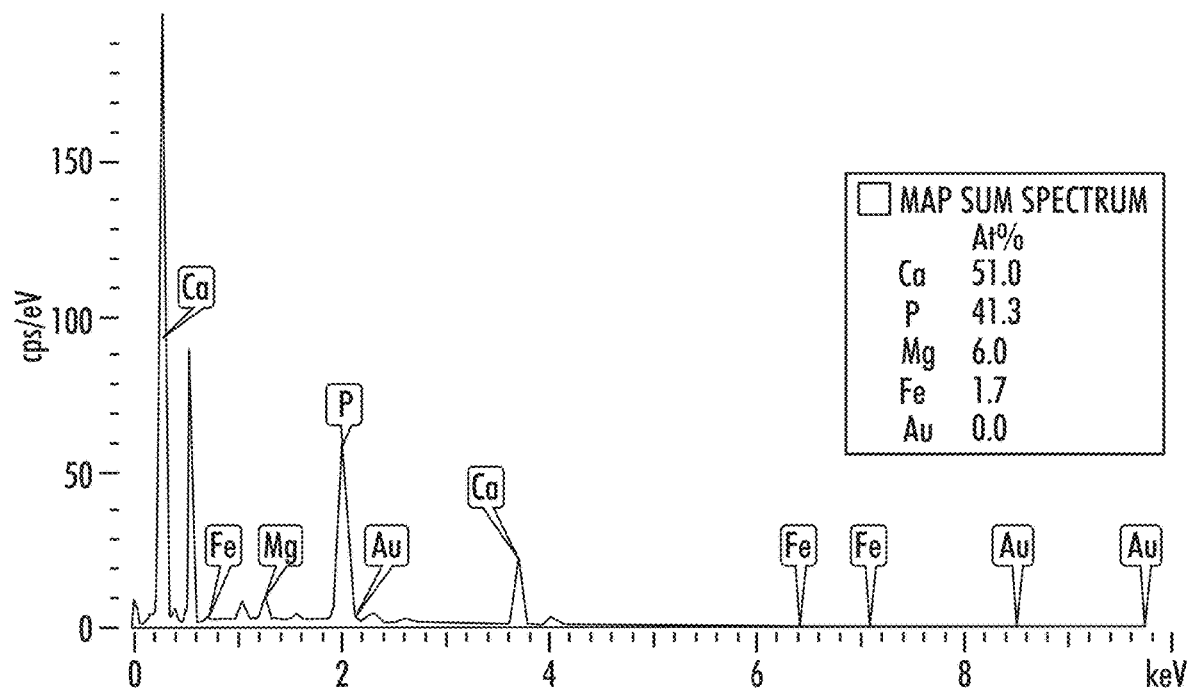
FIG. 26B is a graphical representation of SEM/EDS showing mineralization levels of hASC cells after RF activation of $AuFe_3O_4$ nanoparticles with miRN-148b attached with a furan-based Diels-Alder linker.

Moreover, FIGS. 26A and 26B shows scanning electron microscope/energy dispersive x-ray spectroscopy (SEM/EDS) data on the mineralization effects in hASCs cells transfected with AuFe$_3$O$_4$ nanoparticles with miRN-148b attached with a furan-based Diels-Alder linker. FIG. 26A shows mineralization levels of hASC cells with RF Activated AuFe3O4 nanoparticles without miRN-148b. FIG. 26B shows mineralization levels of hASC cells after RF activation of AuFe$_3$O$_4$ nanoparticles with miRN-148b attached with a furan-based Diels-Alder linker. Comparison of FIG. 26A with FIG. 26B shows that after activation of the composition and release of the therapeutic agent, the hASC cells display increased levels of various minerals, such as calcium and phosphorus.

Various embodiments of the invention have been described in fulfillment of the various objectives of the invention. It should be recognized that these embodiments are merely illustrative of the principles of the invention. Numerous modifications and adaptations thereof will be readily apparent to those skilled in the art without departing from the spirit and scope of the invention.

The invention claimed is:

1. A composition suitable for in vivo administration to a subject comprising:
   a metal nanoparticle;
   a therapeutic species; and
   a linker joining the metal nanoparticle to the therapeutic species,
   wherein the linker comprises a Diels-Alder cyclo-addition reaction product,
   wherein the Diels-Alder cyclo-addition reaction product has a retro Diels-Alder reaction activation temperature between 30° C. and 180° C.,
   wherein the metal nanoparticle has a plasmon resonance frequency in a visible region, in a near infrared region, or in an infrared region of the electromagnetic spectrum, such that upon administration of the composition to a biological compartment of the subject and applying to the biological compartment a wavelength of light matching the plasmon resonance frequency of the metal nanoparticle, the retro Diels-Alder reaction activation temperature is achieved resulting in a retro Diels-Alder reaction that cleaves the linker and releases the therapeutic species in the biological compartment of the subject.

2. The composition of claim 1, wherein the metal nanoparticle is formed from iron, nickel, cobalt, manganese, platinum, silver or gold.

3. The composition of claim 1, wherein the metal nanoparticle comprises at least two of silver, gold, and platinum.

4. The composition of claim 1, wherein the therapeutic species comprises a small molecule, antibiotic, antifungal, nucleic acid, peptide, protein, or combinations thereof.

5. The composition of claim 4, wherein the therapeutic species is a nucleic acid comprising a plasmid, small interfering RNA, micro-RNA, a miRNA mimic, or a combination thereof.

6. The composition of claim 1, wherein the therapeutic species is an osteogenic modulator, a chondrogenic modulator, an endotheliogenic modulator, a myogenic modulator, or an anti-cancer agent.

7. The composition of claim 1, wherein the linker is covalently bonded to the metal nanoparticle.

8. The composition of claim 1, wherein the linker is covalently bonded to the therapeutic species.

9. The composition of claim 1, wherein the Diels-Alder cyclo-addition reaction product is a reaction product of a dienophile and a furan.

10. The composition of claim 1, wherein the Diels-Alder cyclo-addition reaction product is a reaction product of a dienophile and a thiophene.

11. The composition of claim 1, wherein the Diels-Alder cyclo-addition reaction product is a reaction product of a dienophile and a pyrrole.

12. The composition of claim 1, wherein the Diels-Alder cyclo-addition reaction product has a retro Diels-Alder reaction activation temperature between 40° C. and 85° C.

13. The composition of claim 1, wherein the therapeutic species comprises miRNA-148b, a miRNA mimic of miRNA-148b, or a combination thereof.

14. The composition of claim 1, wherein the therapeutic species comprises miRNA-34, a miRNA mimic of miRNA-34, or a combination thereof.

15. The composition of claim 1, wherein the composition is suitable for use in treating or diagnosing a cancer, wherein the cancer is a prostate cancer, a skin cancer, or a lung cancer.

16. The composition of claim 1, wherein the composition is suitable for use in treating or diagnosing a skin cancer.

17. The composition of claim 1, wherein the composition is suitable for use in treating or diagnosing a lung cancer, wherein the lung cancer is a Ras-induced lung cancer.

18. The composition of claim 1, wherein the therapeutic species comprises Paclitaxil, Afatinib, Dimaleate, Bortezomib, Carfilzomib, Doxorubicin, Fluorouracil, a miRNA mimic of miRNA-148b, a miRNA mimic of miRNA-135, a miRNA mimic of miRNA-124, a miRNA mimic of miRNA-101, a miRNA mimic of miRNA-29c, a miRNA mimic of miRNA-15a, a miRNA mimic of miRNA-34, or a combination thereof.

19. The composition of claim 1, wherein the therapeutic species comprises simvastatin, strontium ranelate, miRNA 26a, miRNA 148b, miRNA 27a, miRNA 489, miR-9, miR-140, miR-30A, miR-210, miR-195, miR-155, miR-106b, miR-93, miR-25, miR-206, miR-1, siGDF-8, miR-133, miR-24 or miR-16.

20. The composition of claim 1, wherein the therapeutic species are attached by two or more different linkers comprising different Diels-Alder cyclo-addition products.

* * * * *